United States Patent
Dong et al.

(10) Patent No.: US 11,759,323 B2
(45) Date of Patent: *Sep. 19, 2023

(54) SURFACE MODIFIED UNIT CELL LATTICE STRUCTURES FOR OPTIMIZED SECURE FREEFORM FABRICATION

(71) Applicants: Howmedica Osteonics Corp., Mahwah, NJ (US); The University Of Liverpool, Liverpool (GB)

(72) Inventors: Nicholas Nai Guang Dong, Little Falls, NJ (US); Matthew P. Poggie, Montclair, NJ (US); Robert W. Klein, Orangeburg, NY (US); Eric Jones, Limerick (IE); Christopher J. Sutcliffe, Liverpool (GB); Joseph Robinson, Ridgewood, NJ (US); Dan Jones, Limerick (IE); Lewis Mullen, Englewood, NJ (US); Robin Stamp, Montclair, NJ (US)

(73) Assignees: Howmedica Osteonics Corp., Mahwah, NJ (US); The University Of Liverpool (GB)

( * ) Notice: Subject to any disclaimer, the term of this patent is extended or adjusted under 35 U.S.C. 154(b) by 573 days.

This patent is subject to a terminal disclaimer.

(21) Appl. No.: 16/804,740

(22) Filed: Feb. 28, 2020

(65) Prior Publication Data
US 2020/0202043 A1    Jun. 25, 2020

Related U.S. Application Data

(63) Continuation of application No. 14/877,548, filed on Oct. 7, 2015, now Pat. No. 10,614,176, which is a
(Continued)

(51) Int. Cl.
*A61F 2/30*    (2006.01)
*G06F 30/00*    (2020.01)
(Continued)

(52) U.S. Cl.
CPC ............ *A61F 2/30767* (2013.01); *A61F 2/28* (2013.01); *A61F 2/30942* (2013.01);
(Continued)

(58) Field of Classification Search
CPC ......... G06F 30/00; B33Y 50/00; B33Y 80/00; B23K 26/342; B23K 15/0086
See application file for complete search history.

(56) References Cited

U.S. PATENT DOCUMENTS 14,403 A    3/1856   Brown et al.
222,687 A   12/1879  Fresco
(Continued)

FOREIGN PATENT DOCUMENTS

CA    2295896 A1    7/2000
CA    2448592 A1    5/2004
(Continued)

OTHER PUBLICATIONS

Australian Examination Report for Application No. 2013202075 dated Feb. 13, 2015.
(Continued)

*Primary Examiner* — Bijan Mapar
(74) *Attorney, Agent, or Firm* — Lerner David LLP

(57) ABSTRACT

Aspects of the present disclosure relate generally to preparing models of three-dimensional structures. In particular, a model of a three-dimensional structure constructed of porous geometries is prepared. A component file including a porous CAD volume having a boundary is prepared. A space including the porous CAD volume is populated with unit cells. The unit cells are populated with porous geometries having a plurality of struts having nodes on each end. The space is populated with at least one elongated fixation
(Continued)

element extending beyond the boundary to produce an interlocking feature enabling assembly or engagement with a mating structure.

14 Claims, 21 Drawing Sheets

Related U.S. Application Data continuation of application No. 13/618,218, filed on Sep. 14, 2012, now Pat. No. 9,180,010, which is a continuation-in-part of application No. 13/441,154, filed on Apr. 6, 2012, now Pat. No. 9,135,374.

(51) Int. Cl.
| | | |
|---|---|---|
| *B33Y 50/00* | (2015.01) | |
| *B22F 10/80* | (2021.01) | |
| *B33Y 80/00* | (2015.01) | |
| *B22F 10/28* | (2021.01) | |
| *A61F 2/28* | (2006.01) | |
| *B23K 26/342* | (2014.01) | |
| *B23K 15/00* | (2006.01) | |

(52) U.S. Cl.
CPC .............. *B22F 10/28* (2021.01); *B22F 10/80* (2021.01); *B23K 15/0086* (2013.01); *B23K 26/342* (2015.10); *B33Y 50/00* (2014.12); *G06F 30/00* (2020.01); *A61F 2002/30952* (2013.01); *B33Y 80/00* (2014.12); *Y02P 10/25* (2015.11)

(56) References Cited

U.S. PATENT DOCUMENTS

| | | |
|---|---|---|
| 2,373,769 A | 4/1945 | Macy |
| 3,520,099 A | 7/1970 | Mattes |
| 3,556,918 A | 1/1971 | Lemelson |
| 3,605,123 A | 9/1971 | Pratt et al. |
| 3,806,961 A | 4/1974 | Muller |
| 3,816,855 A | 6/1974 | Saleh |
| 3,826,054 A | 7/1974 | Culpepper, Jr. |
| 4,047,349 A | 9/1977 | Aguilar, Jr. |
| 4,085,466 A | 4/1978 | Goodfellow et al. |
| 4,117,302 A | 9/1978 | Earle et al. |
| 4,154,040 A | 5/1979 | Pace |
| 4,164,794 A | 8/1979 | Spector et al. |
| 4,202,055 A | 5/1980 | Reiner et al. |
| 4,218,494 A | 8/1980 | Belmondo et al. |
| 4,247,508 A | 1/1981 | Housholder |
| 4,305,340 A | 12/1981 | Iwaki et al. |
| 4,344,193 A | 8/1982 | Kenny |
| 4,385,404 A | 5/1983 | Sully et al. |
| 4,444,818 A | 4/1984 | Tominaga et al. |
| 4,479,271 A | 10/1984 | Bolesky et al. |
| 4,502,161 A | 3/1985 | Wall |
| 4,513,045 A | 4/1985 | Bondoc et al. |
| 4,542,539 A | 9/1985 | Rowe, Jr. et al. |
| 4,543,158 A | 9/1985 | Bondoc et al. |
| 4,636,219 A | 1/1987 | Pratt et al. |
| 4,644,942 A | 2/1987 | Sump |
| 4,659,331 A | 4/1987 | Matthews et al. |
| 4,673,408 A | 6/1987 | Grobbelaar |
| 4,673,409 A | 6/1987 | Van Kampen |
| 4,714,473 A | 12/1987 | Bloebaum |
| 4,714,474 A | 12/1987 | Brooks, Jr. et al. |
| 4,719,908 A | 1/1988 | Averill et al. |
| 4,766,029 A | 8/1988 | Brock et al. |
| 4,863,538 A | 9/1989 | Deckard |
| 4,944,817 A | 7/1990 | Bourell et al. |
| 4,961,154 A | 10/1990 | Pomerantz et al. |
| 4,969,302 A | 11/1990 | Coggan et al. |
| 4,969,907 A | 11/1990 | Koch et al. |
| 4,978,355 A | 12/1990 | Frey et al. |
| 4,990,163 A | 2/1991 | Ducheyne et al. |
| 4,997,445 A | 3/1991 | Hodorek |
| 5,002,572 A | 3/1991 | Picha |
| 5,004,476 A | 4/1991 | Cook |
| 5,017,753 A | 5/1991 | Deckard |
| 5,024,670 A | 6/1991 | Smith et al. |
| 5,031,120 A | 7/1991 | Pomerantz et al. |
| 5,034,186 A | 7/1991 | Shimamune et al. |
| 5,053,090 A | 10/1991 | Beaman et al. |
| 5,067,964 A | 11/1991 | Richmond et al. |
| 5,076,869 A | 12/1991 | Bourell et al. |
| 5,080,674 A | 1/1992 | Jacobs et al. |
| 5,090,174 A | 2/1992 | Fragale |
| 5,108,432 A | 4/1992 | Gustavson |
| 5,108,441 A | 4/1992 | McDowell |
| 5,147,402 A | 9/1992 | Bohler et al. |
| 5,155,324 A | 10/1992 | Deckard et al. |
| 5,158,574 A | 10/1992 | Stone |
| 5,171,282 A | 12/1992 | Pequignot |
| 5,176,710 A | 1/1993 | Hahn et al. |
| 5,192,328 A | 3/1993 | Winters |
| 5,219,362 A | 6/1993 | Tuke et al. |
| 5,282,861 A | 2/1994 | Kaplan |
| 5,282,870 A | 2/1994 | Moser et al. |
| 5,287,435 A | 2/1994 | Cohen et al. |
| 5,298,115 A | 3/1994 | Leonard |
| 5,314,478 A | 5/1994 | Oka et al. |
| 5,323,954 A | 6/1994 | Shetty et al. |
| 5,336,518 A | 8/1994 | Narayanan et al. |
| 5,352,405 A | 10/1994 | Beaman et al. |
| 5,356,433 A | 10/1994 | Rowland et al. |
| 5,358,529 A | 10/1994 | Davidson |
| 5,368,602 A | 11/1994 | de la Torre |
| 5,386,500 A | 1/1995 | Pomerantz et al. |
| 5,398,193 A | 3/1995 | deAngelis |
| 5,425,210 A | 6/1995 | Zafir |
| 5,443,510 A | 8/1995 | Shetty et al. |
| 5,443,518 A | 8/1995 | Insall |
| 5,461,839 A | 10/1995 | Beck |
| 5,486,599 A | 1/1996 | Saunders et al. |
| 5,490,962 A | 2/1996 | Cima et al. |
| 5,496,372 A | 3/1996 | Hamamoto et al. |
| 5,504,300 A | 4/1996 | Devanathan et al. |
| 5,507,815 A | 4/1996 | Wagner et al. |
| 5,514,183 A | 5/1996 | Epstein et al. |
| 5,518,680 A | 5/1996 | Cima et al. |
| 5,526,627 A | 6/1996 | Beck |
| 5,549,700 A | 8/1996 | Graham et al. |
| 5,571,185 A | 11/1996 | Schug |
| 5,571,196 A | 11/1996 | Stein |
| 5,580,353 A | 12/1996 | Mendes et al. |
| 5,609,646 A | 3/1997 | Field et al. |
| 5,616,294 A | 4/1997 | Deckard |
| 5,624,463 A | 4/1997 | Stone et al. |
| 5,632,745 A | 5/1997 | Schwartz |
| 5,640,667 A | 6/1997 | Freitag et al. |
| 5,648,450 A | 7/1997 | Dickens, Jr. et al. |
| 5,665,118 A | 9/1997 | LaSalle et al. |
| 5,681,354 A | 10/1997 | Eckhoff |
| 5,702,448 A | 12/1997 | Buechel et al. |
| 5,716,358 A | 2/1998 | Ochoa et al. |
| 5,728,162 A | 3/1998 | Eckhoff |
| 5,729,946 A | 3/1998 | Beck |
| 5,735,903 A | 4/1998 | Li et al. |
| 5,749,874 A | 5/1998 | Schwartz |
| 5,769,899 A | 6/1998 | Schwartz et al. |
| 5,773,789 A | 6/1998 | Devanathan et al. |
| 5,776,201 A | 7/1998 | Colleran et al. |
| 5,782,908 A | 7/1998 | Cahalan et al. |
| 5,795,353 A | 8/1998 | Felt |
| 5,824,098 A | 10/1998 | Stein |
| 5,824,102 A | 10/1998 | Buscayret |
| 5,839,247 A | 11/1998 | Beck |
| 5,857,303 A | 1/1999 | Beck et al. |
| 5,866,113 A | 2/1999 | Hendriks et al. |
| 5,879,387 A | 3/1999 | Jones et al. |
| 5,879,398 A | 3/1999 | Swarts et al. |
| 5,928,285 A | 7/1999 | Bigliani et al. |

(56) References Cited

U.S. PATENT DOCUMENTS

| | | |
|---|---|---|
| 5,973,222 A | 10/1999 | Devanathan et al. |
| 5,987,838 A | 11/1999 | Beck |
| 5,989,472 A | 11/1999 | Ashby et al. |
| 6,013,855 A | 1/2000 | McPherson et al. |
| 6,042,774 A | 3/2000 | Wilkening et al. |
| 6,046,426 A | 4/2000 | Jeantette et al. |
| 6,049,054 A | 4/2000 | Panchison et al. |
| 6,087,553 A | 7/2000 | Cohen et al. |
| 6,096,043 A | 8/2000 | Techiera et al. |
| 6,128,866 A | 10/2000 | Wearne |
| 6,132,468 A | 10/2000 | Mansmann |
| 6,139,585 A | 10/2000 | Li |
| 6,149,689 A | 11/2000 | Grundei |
| 6,164,032 A | 12/2000 | Beck |
| 6,171,340 B1 | 1/2001 | McDowell |
| 6,190,407 B1 | 2/2001 | Ogle et al. |
| 6,206,924 B1 | 3/2001 | Timm |
| 6,206,927 B1 | 3/2001 | Fell et al. |
| 6,215,093 B1 | 4/2001 | Meiners et al. |
| 6,217,615 B1 | 4/2001 | Sioshansi et al. |
| 6,248,131 B1 | 6/2001 | Felt et al. |
| 6,251,143 B1 | 6/2001 | Schwartz et al. |
| 6,261,322 B1 | 7/2001 | Despres, III et al. |
| 6,261,493 B1 | 7/2001 | Gaylo et al. |
| 6,280,478 B1 | 8/2001 | Richter et al. |
| 6,283,997 B1 | 9/2001 | Garg et al. |
| 6,290,726 B1 | 9/2001 | Pope et al. |
| 6,299,645 B1 | 10/2001 | Ogden |
| 6,344,061 B1 | 2/2002 | Leitao et al. |
| 6,355,086 B2 | 3/2002 | Brown et al. |
| 6,370,382 B1 | 4/2002 | Kang et al. |
| 6,371,958 B1 | 4/2002 | Dveraker |
| 6,385,585 B1 | 5/2002 | Jonsson et al. |
| 6,395,327 B1 | 5/2002 | Shetty |
| 6,406,497 B2 | 6/2002 | Takei |
| 6,415,574 B2 | 7/2002 | Beck |
| 6,454,811 B1 | 9/2002 | Sherwood et al. |
| 6,476,343 B2 | 11/2002 | Keicher et al. |
| 6,482,209 B1 | 11/2002 | Engh et al. |
| 6,494,914 B2 | 12/2002 | Brown et al. |
| 6,497,728 B2 | 12/2002 | Yong |
| 6,520,996 B1 | 2/2003 | Manasas et al. |
| 6,530,951 B1 | 3/2003 | Bates et al. |
| 6,551,608 B2 | 4/2003 | Yao |
| 6,558,421 B1 | 5/2003 | Fell et al. |
| 6,582,715 B1 | 6/2003 | Barry et al. |
| 6,589,283 B1 | 7/2003 | Metzger et al. |
| 6,592,598 B2 | 7/2003 | Vibe-Hansen et al. |
| 6,599,301 B2 | 7/2003 | Vibe-Hansen et al. |
| 6,599,322 B1 | 7/2003 | Amrich et al. |
| 6,610,067 B2 | 8/2003 | Tallarida et al. |
| 6,626,945 B2 | 9/2003 | Simon et al. |
| 6,632,246 B1 | 10/2003 | Simon et al. |
| 6,652,246 B1 | 11/2003 | Lin et al. |
| 6,652,587 B2 | 11/2003 | Felt et al. |
| 6,676,892 B2 | 1/2004 | Das et al. |
| 6,679,917 B2 | 1/2004 | Ek |
| 6,682,567 B1 | 1/2004 | Schroeder |
| 6,686,437 B2 | 2/2004 | Buchman et al. |
| 6,699,252 B2 | 3/2004 | Farr, II et al. |
| 6,709,462 B2 | 3/2004 | Hanssen |
| 6,712,822 B2 | 3/2004 | Re et al. |
| 6,712,856 B1 | 3/2004 | Carignan et al. |
| 6,716,957 B2 | 4/2004 | Tunc |
| 6,743,232 B2 | 6/2004 | Overaker et al. |
| 6,770,099 B2 | 8/2004 | Andriacchi et al. |
| 6,802,864 B2 | 10/2004 | Tornier |
| 6,846,329 B2 | 1/2005 | McMinn |
| 6,850,125 B2 | 2/2005 | Norman et al. |
| 6,852,125 B2 | 2/2005 | Simon et al. |
| 6,855,165 B2 | 2/2005 | Fell et al. |
| 6,863,689 B2 | 3/2005 | Ralph et al. |
| 6,866,684 B2 | 3/2005 | Fell et al. |
| 6,893,463 B2 | 5/2005 | Fell et al. |
| 6,911,044 B2 | 6/2005 | Fell et al. |
| 6,916,341 B2 | 7/2005 | Rolston |
| 6,921,264 B2 | 7/2005 | Mayer et al. |
| 6,923,831 B2 | 8/2005 | Fell et al. |
| 6,932,610 B2 | 8/2005 | Ono et al. |
| 7,051,417 B2 | 5/2006 | Michelson |
| 7,168,283 B2 | 1/2007 | Van Note et al. |
| 7,294,149 B2 | 11/2007 | Hozack et al. |
| 7,388,972 B2 | 6/2008 | Kitson |
| 7,494,507 B2 | 2/2009 | Dixon et al. |
| 7,497,876 B2 | 3/2009 | Tuke et al. |
| 7,521,017 B2 | 4/2009 | Kunze et al. |
| 7,537,664 B2 | 5/2009 | O'Neill et al. |
| 7,563,284 B2 | 7/2009 | Coppes et al. |
| 7,632,575 B2 | 12/2009 | Justin et al. |
| 7,637,942 B2 | 12/2009 | Mangiardi et al. |
| 7,655,047 B2 | 2/2010 | Swords |
| 7,674,517 B2 | 3/2010 | Ramsey et al. |
| 7,718,109 B2 | 5/2010 | Robb et al. |
| 7,747,305 B2 | 6/2010 | Dean et al. |
| 7,879,275 B2 | 2/2011 | Smith et al. |
| 8,275,594 B2 | 9/2012 | Lin et al. |
| 8,308,807 B2 | 11/2012 | Seebeck et al. |
| 8,350,186 B2 | 1/2013 | Jones et al. |
| 8,430,930 B2 | 4/2013 | Hunt |
| 8,454,705 B2 | 6/2013 | Pressacco et al. |
| 8,551,173 B2 | 10/2013 | Lechmann et al. |
| 8,728,387 B2 | 5/2014 | Jones et al. |
| 8,828,087 B2 | 9/2014 | Stone et al. |
| 8,843,229 B2 | 9/2014 | Vanasse et al. |
| 8,888,862 B2 | 11/2014 | McDonnell et al. |
| 8,903,533 B2 | 12/2014 | Eggers et al. |
| 8,956,364 B2 | 2/2015 | Catanzarite et al. |
| 8,979,936 B2 | 3/2015 | White et al. |
| 8,983,646 B1 | 3/2015 | Hanna |
| 9,011,444 B2 | 4/2015 | Primiano et al. |
| 9,060,788 B2 | 6/2015 | Bollinger |
| 9,066,734 B2 | 6/2015 | Schoenefeld et al. |
| 9,084,618 B2 | 7/2015 | Serbousek et al. |
| 9,113,971 B2 | 8/2015 | Metzger et al. |
| 9,135,374 B2 | 9/2015 | Jones et al. |
| 9,149,282 B2 | 10/2015 | Servidio et al. |
| 9,173,661 B2 | 11/2015 | Metzger et al. |
| 9,173,666 B2 | 11/2015 | Metzger et al. |
| 9,180,010 B2 | 11/2015 | Dong et al. |
| 9,204,977 B2 | 12/2015 | Bollinger |
| 9,237,950 B2 | 1/2016 | Hensley et al. |
| 9,241,745 B2 | 1/2016 | Smith et al. |
| 9,271,744 B2 | 3/2016 | Meridew |
| 9,289,253 B2 | 3/2016 | Vanasse et al. |
| 9,295,497 B2 | 3/2016 | Schoenefeld et al. |
| 9,301,812 B2 | 4/2016 | Kehres et al. |
| 9,339,278 B2 | 5/2016 | Meridew et al. |
| 9,345,548 B2 | 5/2016 | Schoenefeld et al. |
| 9,351,743 B2 | 5/2016 | Kehres et al. |
| 9,364,330 B2 | 6/2016 | Lindsey et al. |
| 9,386,993 B2 | 7/2016 | Meridew et al. |
| 9,393,028 B2 | 7/2016 | Schuster |
| 9,408,616 B2 | 8/2016 | Kehres et al. |
| 9,427,320 B2 | 8/2016 | Meridew |
| 9,439,659 B2 | 9/2016 | Schoenefeld et al. |
| 9,445,907 B2 | 9/2016 | Meridew et al. |
| 9,451,973 B2 | 9/2016 | Heilman et al. |
| 9,456,833 B2 | 10/2016 | Maxson et al. |
| 9,456,901 B2 | 10/2016 | Jones et al. |
| 9,814,595 B2 | 11/2017 | Biedermann et al. |
| 10,166,316 B2 | 1/2019 | Landon et al. |
| 2001/0014403 A1 | 8/2001 | Brown et al. |
| 2002/0010512 A1 | 1/2002 | Takei |
| 2002/0015654 A1 | 2/2002 | Das et al. |
| 2002/0016635 A1 | 2/2002 | Despres et al. |
| 2002/0127328 A1 | 9/2002 | Shetty |
| 2002/0130112 A1 | 9/2002 | Manasas et al. |
| 2002/0151983 A1 | 10/2002 | Shetty |
| 2002/0173855 A1 | 11/2002 | Mansmann |
| 2002/0198528 A1 | 12/2002 | Engh et al. |
| 2003/0032351 A1 | 2/2003 | Horner et al. |
| 2003/0033018 A1 | 2/2003 | Merchant |
| 2003/0045941 A1 | 3/2003 | Lewallen |
| 2003/0055500 A1 | 3/2003 | Fell et al. |

(56) References Cited

U.S. PATENT DOCUMENTS

| | | |
|---|---|---|
| 2003/0055501 A1 | 3/2003 | Fell et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0060888 A1 | 3/2003 | Fell et al. |
| 2003/0069638 A1 | 4/2003 | Barlow et al. |
| 2003/0069718 A1 | 4/2003 | Hollister et al. |
| 2003/0153977 A1 | 8/2003 | Suguro et al. |
| 2003/0153981 A1 | 8/2003 | Wang et al. |
| 2003/0155686 A1 | 8/2003 | Hawkins et al. |
| 2003/0158606 A1 | 8/2003 | Coon et al. |
| 2003/0209305 A1 | 11/2003 | Smith et al. |
| 2003/0220696 A1 | 11/2003 | Levine et al. |
| 2004/0000540 A1 | 1/2004 | Soboyejo et al. |
| 2004/0006393 A1 | 1/2004 | Burkinshaw |
| 2004/0009228 A1 | 1/2004 | Tormala et al. |
| 2004/0015170 A1 | 1/2004 | Tallarida et al. |
| 2004/0023586 A1 | 2/2004 | Tilton |
| 2004/0044414 A1 | 3/2004 | Nowakowski |
| 2004/0054416 A1 | 3/2004 | Wyss et al. |
| 2004/0059356 A1 | 3/2004 | Gingras |
| 2004/0098132 A1 | 5/2004 | Andriacchi et al. |
| 2004/0121110 A1 | 6/2004 | Schmidt et al. |
| 2004/0143339 A1 | 7/2004 | Axelson et al. |
| 2004/0148030 A1 | 7/2004 | Ek |
| 2004/0153163 A1 | 8/2004 | Posner |
| 2004/0162622 A1 | 8/2004 | Simon et al. |
| 2004/0167633 A1 | 8/2004 | Wen et al. |
| 2004/0191106 A1 | 9/2004 | O'Neill et al. |
| 2004/0199249 A1 | 10/2004 | Fell |
| 2004/0199250 A1 | 10/2004 | Fell |
| 2004/0204766 A1 | 10/2004 | Siebel |
| 2004/0230315 A1 | 11/2004 | Ek |
| 2004/0243237 A1 | 12/2004 | Unwin et al. |
| 2004/0267363 A1 | 12/2004 | Fell et al. |
| 2005/0033424 A1 | 2/2005 | Fell |
| 2005/0043816 A1 | 2/2005 | Datta et al. |
| 2005/0079200 A1 | 4/2005 | Rathenow et al. |
| 2005/0085918 A1 | 4/2005 | Soffiati et al. |
| 2005/0100578 A1 | 5/2005 | Schmid et al. |
| 2005/0123672 A1 | 6/2005 | Justin et al. |
| 2005/0154471 A1 | 7/2005 | Aram et al. |
| 2005/0170159 A1 | 8/2005 | Ramsey et al. |
| 2005/0171604 A1 | 8/2005 | Michalow |
| 2005/0177169 A1 | 8/2005 | Fisher et al. |
| 2005/0192672 A1 | 9/2005 | Wyss et al. |
| 2006/0015187 A1 | 1/2006 | Hunter et al. |
| 2006/0036331 A1 | 2/2006 | Lu et al. |
| 2006/0045903 A1 | 3/2006 | Kadiyala et al. |
| 2006/0147332 A1 | 7/2006 | Jones et al. |
| 2006/0241776 A1 | 10/2006 | Brown et al. |
| 2006/0254200 A1 | 11/2006 | Clarke et al. |
| 2007/0142914 A1 | 6/2007 | Jones et al. |
| 2007/0156249 A1 | 7/2007 | Lawrynowicz et al. |
| 2007/0225390 A1 | 9/2007 | Wang et al. |
| 2008/0004709 A1 | 1/2008 | O'Neill et al. |
| 2008/0050412 A1 | 2/2008 | Jones et al. |
| 2008/0161927 A1 | 7/2008 | Savage et al. |
| 2009/0068245 A1 | 3/2009 | Noble et al. |
| 2009/0087605 A1 | 4/2009 | Ramsey et al. |
| 2009/0105772 A1 | 4/2009 | Seebeck et al. |
| 2009/0112315 A1 | 4/2009 | Fang et al. |
| 2010/0057211 A1 | 3/2010 | Cuckler et al. |
| 2010/0298950 A1 | 11/2010 | McDonnell et al. |
| 2011/0014081 A1 | 1/2011 | Jones et al. |
| 2011/0313532 A1 | 12/2011 | Hunt |
| 2012/0067853 A1 | 3/2012 | Wang et al. |
| 2013/0030529 A1 | 1/2013 | Hunt |
| 2013/0056912 A1 | 3/2013 | O'Neill et al. |
| 2013/0123935 A1 | 5/2013 | Hunt et al. |
| 2013/0158672 A1 | 6/2013 | Hunt |
| 2013/0218282 A1 | 8/2013 | Hunt |
| 2013/0264749 A1 | 10/2013 | Jones et al. |
| 2013/0268085 A1 | 10/2013 | Dong et al. |
| 2013/0331949 A1 | 12/2013 | Dehoff et al. |
| 2014/0037873 A1 | 2/2014 | Cheung et al. |
| 2014/0058526 A1 | 2/2014 | Meridew et al. |
| 2014/0121776 A1 | 5/2014 | Hunt |
| 2014/0163445 A1 | 6/2014 | Pallari et al. |
| 2014/0277548 A1 | 9/2014 | Cohen et al. |
| 2014/0288649 A1 | 9/2014 | Hunt |
| 2014/0288650 A1 | 9/2014 | Hunt |
| 2014/0301884 A1 | 10/2014 | Hellestam et al. |
| 2014/0343681 A1 | 11/2014 | Cohen et al. |
| 2015/0018956 A1 | 1/2015 | Steinmann et al. |
| 2015/0134063 A1 | 5/2015 | Steinmann et al. |
| 2016/0098495 A1 | 4/2016 | Dong et al. |
| 2016/0296672 A1 | 10/2016 | Grohowski, Jr. |

FOREIGN PATENT DOCUMENTS

| | | |
|---|---|---|
| CN | 101301230 A | 11/2008 |
| CN | 102087676 A | 6/2011 |
| DE | 19502733 A1 | 3/1996 |
| EP | 0 178 650 A2 | 4/1986 |
| EP | 0295038 A2 | 12/1988 |
| EP | 0 528 800 A1 | 3/1993 |
| EP | 0761242 A1 | 3/1997 |
| EP | 1247537 A1 | 10/2002 |
| EP | 1 300 511 A2 | 4/2003 |
| EP | 1418013 A1 | 5/2004 |
| EP | 1426013 A1 | 6/2004 |
| EP | 1455666 A1 | 9/2004 |
| EP | 1493455 A2 | 1/2005 |
| EP | 1683593 A2 | 7/2006 |
| EP | 1800700 A2 | 6/2007 |
| EP | 1806154 A1 | 7/2007 |
| EP | 1949989 A1 | 7/2008 |
| EP | 2022622 A1 | 2/2009 |
| EP | 2606859 A1 | 6/2013 |
| JP | 2255329 A | 10/1990 |
| JP | 4041794 A | 2/1992 |
| JP | 11287020 A | 10/1999 |
| JP | 11348045 A | 12/1999 |
| JP | 2001303751 A | 10/2001 |
| JP | 2003293012 A | 10/2003 |
| JP | 2006158953 A | 6/2006 |
| RU | 2218242 C2 | 12/2003 |
| WO | 9606881 A2 | 3/1996 |
| WO | 02085246 A2 | 10/2002 |
| WO | 2005/084216 A2 | 9/2005 |
| WO | 2005080029 A1 | 9/2005 |
| WO | 2005087982 A1 | 9/2005 |
| WO | 2007058160 A1 | 5/2007 |
| WO | 2009116950 A1 | 9/2009 |
| WO | 2011002765 A2 | 1/2011 |
| WO | 2011060312 A2 | 5/2011 |
| WO | 2013006778 A2 | 1/2013 |

OTHER PUBLICATIONS

Australian Examination Report for Application No. 2013202686 date Aug. 7, 2014.

C.K. Chua et al. Development of a Tissue Engineering Scaffold Structure Library for Rapid Prototyping. Parts 1 and 2, International Journal of Advanced Manufacturing Technology, Feb. 2003, vol. 21, pp. 291-312.

Canadian Office Action and Examination Search Report for Appln. No. 2,860,188 dated Jun. 4, 2015.

Chen, "3D Texture Mapping for Rapid Manufacturing", Computer-Aided Design and Applications, University of Southern California, vol. 4, No. 6, pp. 761-771, Jan. 1, 2007.

Created and Designed by Shaman Gaspar, Maintained by Peter Fox, "Direct Laser Remelting", "Project Web Site", Using Lasers to Grow 3D object on Stainless Steel; The University of Liverpool 2002; http://mserc.liv.ac.uk/research/dlr/dlr_html.

Dr. Kerron Harvey, producer, Research Intelligence, The University of Liverpool, Issue 13, Jun. 2002.

Engelbrecht et al., Cellular Structures for Optimal Performance, Georgia Institute of Technology & Paramount Industries, Inc., 2009.

(56) References Cited

OTHER PUBLICATIONS

European Examination Report for Application No. EP10162970.7 dated Dec. 3, 2013.
European Search Report and Written Opinion, EP05028133, dated May 11, 2010.
European Search Report and Written Opinion, EP06127218, dated May 6, 2010.
European Search Report and Written Opinion, EP10162970, dated Jun. 17, 2010.
Extended European Search Report for Application No. EP13162576.6 dated Jul. 4, 2017.
Extended European Search Report for Application No. EP18173165 dated Sep. 18, 2018.
Filiz et al., Int. Journal of Machine Tools & Manufacture, 48, 459-472, 2008.
H.J. Niu and I.T.H. Chang, "Selective Laser Sintering of Gas and Water Atomized High Speed Steel Powders," Scripta Materialia vol. 41, No. 1, (1999), pp. 25-30.
Hawley's Condensed Chemical Dictionary, 14th edition. John Wiley & Sons, 2002. Definition: sintering.
Hollander et al., Structural mechanical and in vitro characterization of individually structured Ti-A1-4V produces by direct layer forming, Biomaterials, pp. 1-9, 2005.
Meiners et al., "Direct Generation of Metal Parts and Tools by Selective Laser Powder Remelting (SLPR)", W. Meiners, C. Over, K. Wissenbach, R. Poprawe, pp. 655-661 Austin, Texas, Aug. 9-11, 1999.
N.K. Vail, L.D. Swain, W.C. fox, T.B. Aufdlemorte, G. Lee, J.W. Barlow, "Materials for biomedical applications," Materials and Design, 20, 1999, pp. 123-132.
Patello-femoral Arthroplasty X-ray Results, Stryker Howmedica Osteonics, published on or before Apr. 5, 2011.
PCT/US2008/008955 International Preliminary Report on Patentability dated Feb. 4, 2010.
PCT/US2008/008955 International Search Report and Written Opinion dated Dec. 2, 2008.
Protek Cementless Replacement of the Acetabulum by E. Morscher, published on or before Apr. 5, 2011.
R. Morgan, C.J. Sutcliffe, W. O'Neill, "Experimental investigatoin of nanosecond pulsed Nd:YAG laser re-melted pre-placed powder beds," Rapid Prototyping Journal, vol. 7, No. 3, 2001, pp. 159-172.
R.H. Morgan, A.J. Papworth, C. Sutcliffe, P. Fox, W. O'Neill, "High density net shape components by direct laser re-melting of single phase powders," Journal of Materials Science, 37, 2002, pp. 3093-3100.
The Metals Handbook, Desk Edition, 2nd Edition, ASM International, 1998, p. 29.
Vureal et al., Plasma-sprayed oxide ceramics on steel substrates, Surface Coatings and Technology, 97 (1997) 347-354.
Wang, Computer-Aided Design Methods for Additive Fabrication of Truss Structures, Georgia Institute of Technology, 2002.
Bobyn et al., "The optimum pore size for the fixation of porous-surfaced metal implants by the ingrowth of bone", Clinical Orthopaedics and Related Research, 150; 263-270 (1980).
Canadian Office Action for Application No. 2,529,884 dated Mar. 27, 2013.
Interlocutory Decision for Application No. EP 06125422.3 dated Nov. 14, 2012.
Notice of Opposition for EP Application No. 06125422.3 dated Jul. 4, 2011.
Amir et al; "Stress-constrained continuum topology optimization: a new approach based on elasto-plasticity" Nov. 6, 2018, 30 pages.
Long et al, "Titanium alloys in total joint replacement-a materials science perspective", Biomaterials 19, Year 1998, pp. 1621-1639.
Randic et al; "Evaluation of the Stress Concentration Factor in Butt Welded Joints: A Comparative Study", Metals 2021, 11, 411, 10 pages.
Stryker Orthopaedics R&D Technical Report; "Porous-Coated Triathlon Tibial Baseplate-A Characterization of the Material Mechanical Properties", D00357-2, Version 5, 123 pages.
Tanzer et al., The Hip Society Supplement To the Bone & Joint Journal ; Characterization of bone ingrowth and interface mechanics of a new porous 3D printed biomaterial; vol. 101-B, No. 6, Jun. 2019 ; pp. 32-67.

FIG. 14a
FIG. 14b
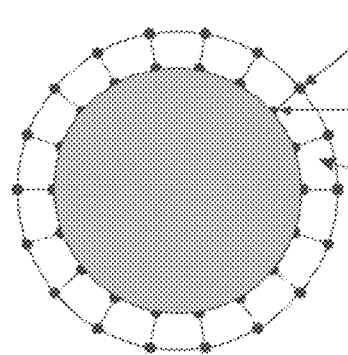
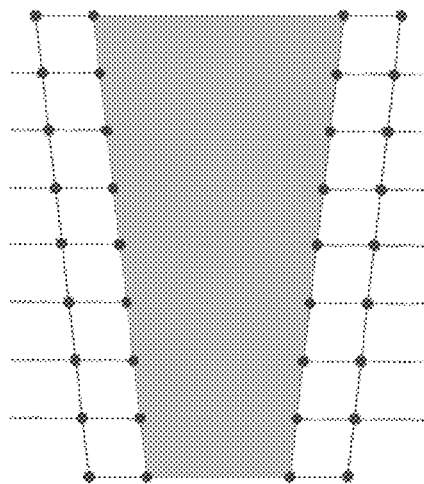
FIG. 15a
FIG. 15b
FIG. 15c
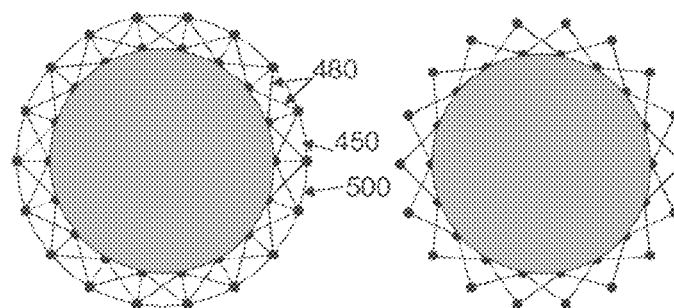
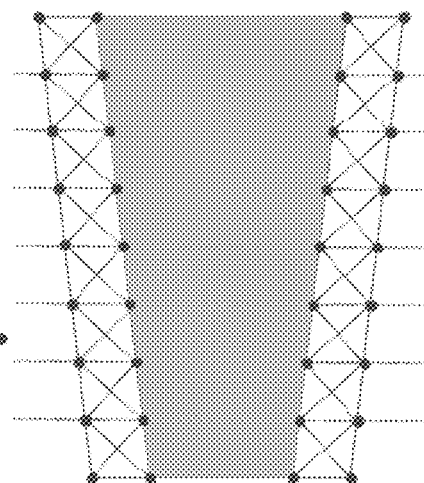

FIG. 35a
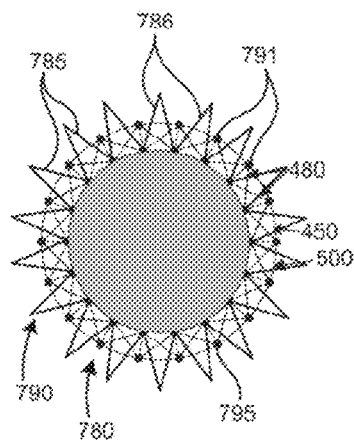
FIG. 35b
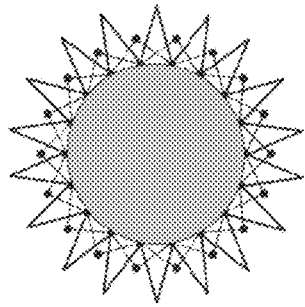
FIG. 35c
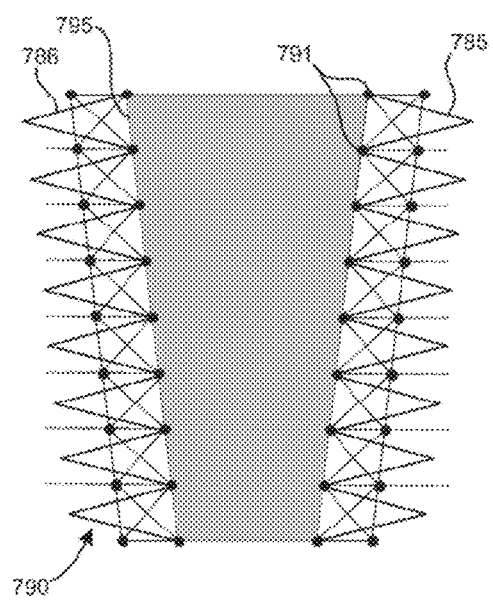
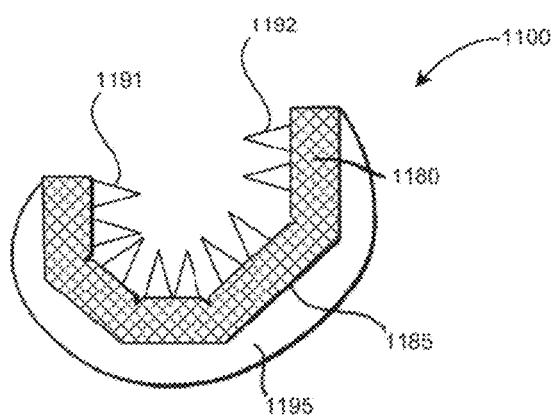
FIG. 36

SURFACE MODIFIED UNIT CELL LATTICE STRUCTURES FOR OPTIMIZED SECURE FREEFORM FABRICATION

CROSS REFERENCE TO RELATED APPLICATIONS

The present application is a continuation of U.S. patent application Ser. No. 14/877,548, filed Oct. 7, 2015, now U.S. Pat. No. 10,614,176, which is a continuation of U.S. patent application Ser. No. 13/618,218, filed Sep. 14, 2012, now U.S. Pat. No. 9,180,010, which is a continuation-in-part of U.S. patent application Ser. No. 13/441,154, filed Apr. 6, 2012, now U.S. Pat. No. 9,135,374, the disclosures of which are incorporated herein by reference.

FIELD OF THE INVENTION

The present invention relates generally to preparing computer-generated models of porous structures. In particular, the surfaces of computer-generated models of structures may be modified through movement and removal of struts and nodes of porous geometries near the surface to produce surfaces conforming to the surfaces of intended physical structures being modeled.

BACKGROUND OF THE INVENTION

The field of free-form fabrication has seen many important recent advances in the fabrication of articles directly from computer controlled databases. These advances, many of which are in the field of rapid prototyping of articles such as prototype parts and mold dies, have greatly reduced the time and expense required to fabricate articles, particularly in contrast to conventional machining processes in which a block of material, such as a metal, is machined according to engineering drawings.

One example of a modern rapid prototyping technology is a selective laser sintering process. According to this technology, articles are produced in layer-wise fashion from a laser-fusible powder that is dispensed one layer at a time. The powder is sintered, by the application of laser energy that is directed in raster-scan fashion to portions of the powder layer corresponding to a cross section of the article. After the sintering of the powder on one particular layer, an additional layer of powder is dispensed, and the process repeated, with sintering taking place between the current layer and the previously laid layers until the article is complete. Detailed descriptions of the selective laser sintering technology may be found in U.S. Pat. Nos. 4,863,538, 5,017,753, 5,076,869 and 4,944,817, the entire disclosures of which are incorporated by reference herein. Similarly, a detailed description of the use of selective laser melting technology may be found in U.S. patent application Ser. No. 10/704,270, filed on Nov. 7, 2003, now U.S. Pat. No. 7,537,664 ("the '664 patent"), the disclosure of which is incorporated by reference herein. The selective laser melting and sintering technologies have enabled the direct manufacture of solid or porous three-dimensional articles of high resolution and dimensional accuracy from a variety of materials including wax, metal powders with binders, polycarbonate, nylon, other plastics and composite materials, such as polymer-coated metals and ceramics.

The invention claimed in the '664 patent was the first of many inventions assigned to Howmedica Osteonics Corporation, who has been a pioneer in porous surface and porous structure formation, specifically for use in orthopedics. For instance, other applications in this area, such as U.S. patent application Ser. No. 11/027,421 filed on Dec. 30, 2004 ("the '421 application"), and U.S. patent application Ser. No. 12/846,327 filed on Jul. 29, 2010 ("the '327 application"), the entire disclosures of which are hereby incorporated by reference herein, have taught the generation of a population of porous geometry, a mathematical representation of the portion of geometry of the porous structure to be built within a region defined by predetermined unit cells or imaginary volumes that are organized to fill and form a predetermined build geometry, or model build structure, which may be used to produce a near net-shape of an intended porous tissue in-growth structure. The predetermined build geometry, or overall computer-aided design (CAD) geometry, may refer to the mathematical or pictorial representation (such as that on a computer display) of the extent or outer boundary of an intended physical structure to be manufactured. In the case of physical components that include both porous material and solid material, the model build structure may be an assembly of solid and porous CAD volumes that model the outer boundaries of the respective solid and porous materials intended to be manufactured. Furthermore, these applications teach the randomization of the position of interconnected nodes, or points of intersection between two struts or between a strut and a substrate, that define each of the porous geometries while maintaining the interconnectivity between the nodes. As previously taught, such randomization may accomplished by changing the coordinate positions of the nodes in the x, y, and z directions of a Cartesian coordinate system, to new positions based on a defined mathematical function. To achieve a required external shape for a device being created, these references have taught the truncation or removal of struts forming the unit cells at the outer surface. Such truncation helps to achieve the near-net shape of the intended structure, but truncated or clipped struts may, in some instances, create a situation where the porous geometries are un-supported by the underlying structures. These truncated struts may present a potential site for the generation of debris as protruding struts may fracture.

Additionally, although modeling structures with porous geometries has become a very useful tool in modern rapid prototyping, models of a porous ingrowth structure may in some instances include a surface that generates an intended structure that, prior to bone ingrowth into the structure, leaves a gap between the porous ingrowth structure and resected bone or other bone structure with which the porous ingrowth structure interfaces. While bone cement may be used at the time of surgery to provide initial stability, the application of such requires additional steps, risks, and time, and may interfere with the intended bone ingrowth capabilities of the surface. Moreover, the mechanical integrity of the cement mantle is dependent upon surgical technique as well as the cement material. Over a long period of time, the cement acts as an additional mechanical structure but adds additional risks due to potential failure within the cement mantle and at both the cement-bone and cement-implant interfaces.

Thus, a new method is needed to create build geometries having surfaces that are more robust and less likely to form debris as well as that provide initial stability that eliminates the need for cement and reduces or eliminates these risks.

SUMMARY OF THE INVENTION

In accordance with an embodiment of the invention, a process of preparing a computer generated model of a three dimensional structure constructed of porous geometries may include a step of preparing a computer-generated component file including a porous CAD volume having a boundary having a predefined portion. The process for preparing the model may include a step of populating, by a processor, a space. The space may include the porous CAD volume which may be populated by unit cells that overlap the predefined portion of the boundary. The process for preparing the model may include a step of populating, by a processor, the unit cells with porous geometries. The porous geometries may have a plurality of struts with nodes at each of the ends of the struts including a first strut overlapping the predefined portion of the boundary. The first strut may have a length, a first node outside the porous CAD volume, and a second node inside the porous CAD volume. The process for preparing the model may include a step of removing all struts entirely outside the porous CAD volume in which after the removal of the struts entirely outside the porous CAD volume, each of the remaining struts is connected to a node at each end of the remaining struts.

In accordance with a further embodiment of the invention, a process of preparing a computer generated model of a three dimensional structure constructed of porous geometries may include a step of preparing a computer-generated component file including a porous CAD volume having a boundary with a predefined portion. The process may include a step of populating, by a processor, a space. The space may include the porous CAD volume which may be populated by unit cells that overlap the predefined portion of the boundary. The process for preparing the model may include a step of populating, by a processor, the unit cells with porous geometries in which the porous geometries have a plurality of struts with nodes at each of the ends of the struts including a first strut that intersects the predefined portion of the boundary. The first strut may have a length and a first node at a first location that may be on the predefined outer boundary or outside the porous CAD volume. The process for preparing the model may include a step of removing all struts entirely outside the porous CAD volume. The process for preparing the model may include a step of moving the first node from the first location to a second location.

In accordance with a further embodiment of the invention, a tangible computer-readable storage medium may have computer readable instructions of a program stored on the medium. The instructions, when executed by a processor, may cause the processor to perform a process of preparing a computer generated model of a three dimensional structure constructed of unit cells. The process of preparing the model may include a step of preparing a computer-generated component file including a porous CAD volume having a boundary having a predefined portion. The process for preparing the model may include a step of populating, by a processor, a space. The space may include the porous CAD volume which may be populated by unit cells that overlap the predefined portion of the boundary. The process for preparing the model may include a step of populating, by a processor, the unit cells with porous geometries. The porous geometries may have a plurality of struts with nodes at each of the ends of the struts including a first strut overlapping the predefined portion of the boundary. The first strut may have a length, a first node outside the porous CAD volume, and a second node inside the porous CAD volume. The process for preparing the model may include a step of removing all struts entirely outside the porous CAD volume in which after the removal of the struts entirely outside the porous CAD volume, each of the remaining struts is connected to a node at each end of the remaining struts.

In accordance with a further embodiment of the invention, a process of preparing a computer-generated model of a three-dimensional structure constructed of porous geometries may include a step of preparing a computer-generated component file including a porous CAD volume having a boundary. The process for preparing the model may include a step of populating, by a processor, a space including the porous CAD volume with unit cells. The process for preparing the model may include a step of populating, by a processor, the unit cells with porous geometries. A plurality of the porous geometries may have a plurality of struts with nodes at each of the ends of the struts. The process for preparing the model may include a step of populating, by a processor, the space with at least one fixation element that may extend beyond the boundary to produce an interlocking feature. Such an interlocking feature may enable assembly or engagement with a mating structure.

In accordance with a further embodiment of the invention, a process of producing a three-dimensional structure may include a step of preparing a computer-generated model of a three-dimensional structure such as in the manner just described. The process of producing the structure may include a step of depositing a metal powder onto a substrate. The process of producing the structure may include a step of scanning a beam onto the deposited metal powder to form a first physical layer of a porous section. The first physical layer may correspond to a portion of a porous CAD volume of the model of the three-dimensional structure. The three-dimensional structure may have a geometric lattice structure constructed of porous geometries and a boundary. The porous geometries may be formed by a plurality of struts. Each of the plurality of struts may have a node on each end of the strut. The process of producing the structure may include a step of repeating the step of depositing the metal powder onto the substrate. The process of producing the structure may include a step of repeating the step of scanning the beam onto the deposited metal powder to form additional physical layers of the three-dimensional structure. The process may include a step of forming an elongated fixation member for assembly or engagement with a mating structure. The fixation member may correspond to the elongated fixation element and may extend beyond the boundary.

In accordance with a further embodiment of the invention, a tangible computer-readable storage medium may have computer readable instructions of a program stored on the medium. The instructions, when executed by a processor, may cause the processor to perform a process of preparing a computer-generated model of a three-dimensional structure constructed of unit cells. The process of preparing the model may include a step of preparing a computer-generated component file including a porous CAD volume having a boundary. The process for preparing the model may include a step of populating, by a processor, a space including the porous CAD volume with unit cells. The process for preparing the model may include a step of populating, by a processor, the unit cells with porous geometries. A plurality of the porous geometries may have a plurality of struts with nodes at each of the ends of the struts. The process for preparing the model may include a step of populating, by a processor, the space with at least one fixation element that may extend beyond the boundary to produce an interlocking feature. Such an interlocking feature may enable assembly or engagement with a mating structure.

BRIEF DESCRIPTION OF THE DRAWINGS

FIG. 2b is a three-dimensional schematic representation of a spatial arrangement of melt spots that may be used to create the porous geometries of FIG. 2a;

FIG. 7b illustrates the nodes of the porous geometries within the unit cells of FIG. 7a.

FIGS. 14a and 14b show plan and side cross-sectional views, respectively, of the tapered cylindrical geometry of FIGS. 13a and 13b, respectively, wherein nodes are populated at corners of unit cells within slices of the porous CAD volume through the use of polar coordinates;

FIGS. 15a-15c show a plan view including unit cells, a plan view without unit cells, and a side cross-sectional view, respectively, of the tapered cylindrical geometry of FIGS. 14a and 14b, wherein struts connecting the nodes have been generated in a conformal manner;

FIGS. 35a-35c show a plan view including unit cells, a plan view without unit cells, and a side cross-sectional view, respectively, of the tapered cylindrical geometry of FIGS. 15a-15c, wherein elongated fixation elements extend from a substrate thereof;

FIG. 36 shows a cross-sectional view of a model build structure of a femoral knee implant having elongated fixation elements extending from a porous CAD volume thereof in accordance with an embodiment of the invention.

DETAILED DESCRIPTION OF THE INVENTION

This invention relates generally to generating computer models of three-dimensional structures. These models may be used to prepare porous tissue in-growth structures in medical implants and prostheses. The models may include features corresponding to tangible structures having nodes along a predefined outer boundary.

Figure 1:
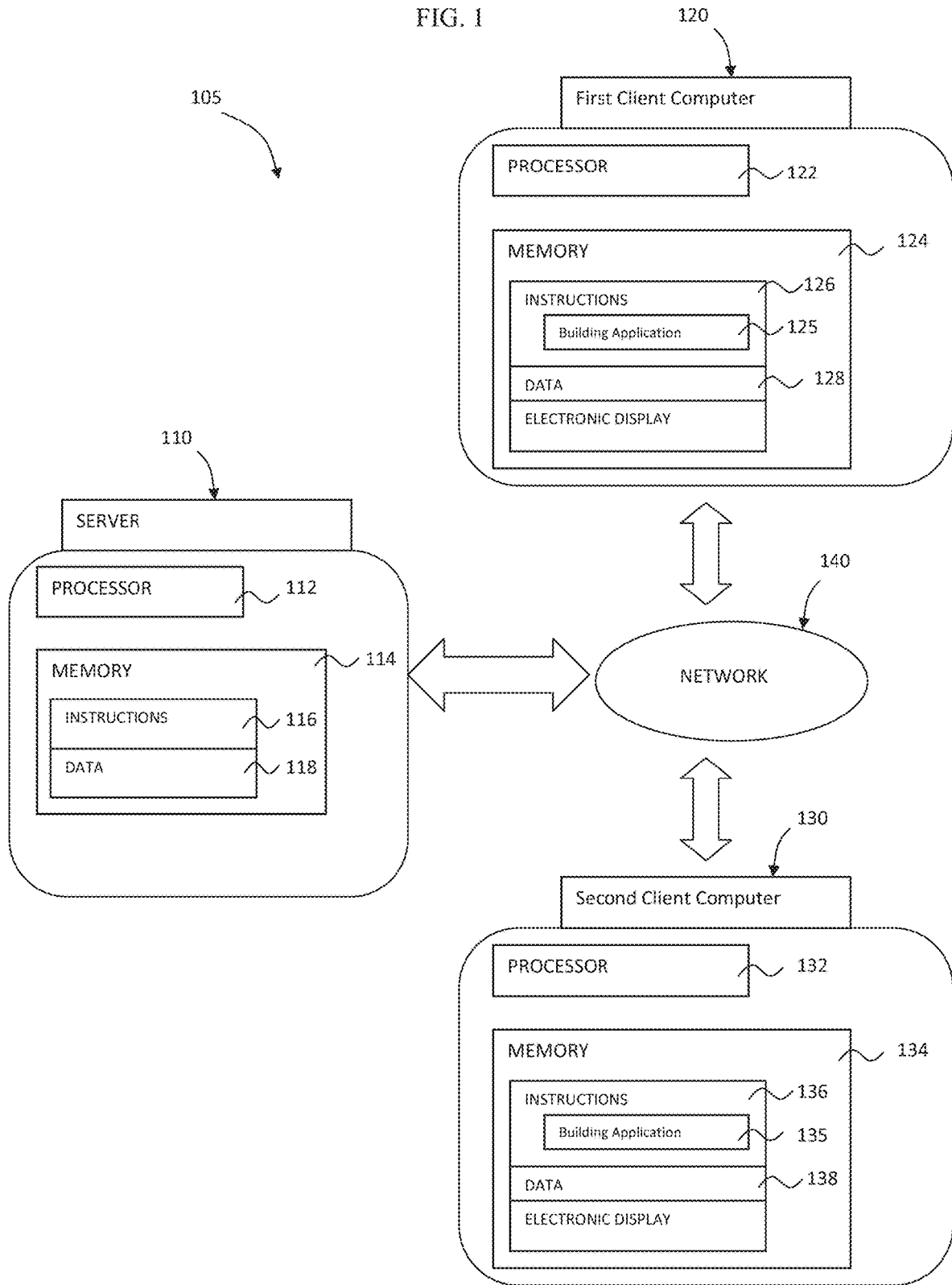
FIG. 1 is a functional diagram of a system in accordance with an exemplary embodiment of the present invention.

FIG. 1 depicts a system 105 that may be used, among other functions, to generate, store and share three-dimensional models of structures. The system 105 may include at least one server computer 110, a first client computer 120, and in some instances, at least a second client computer 130. These computers may send and receive information via a network 140. For example, a first user may generate a model at the first client device 120. The model may then be uploaded to the server 110 and distributed via the network 140 to the second client computer 130 for viewing and modification by at least a second user.

The network 140, and intervening communication points, may comprise various configurations and protocols including the Internet, World Wide Web, intranets, virtual private networks, wide area networks, local networks, private networks using communication protocols proprietary to one or more companies, Ethernet, WiFi and HTTP, and various combinations of the foregoing. Such communication may be facilitated by any device capable of transmitting data to and from other computers, such as modems (e.g., dial-up, cable or fiber optic) and wireless interfaces. Although only a few devices are depicted in FIG. 1, a typical system may include a large number of connected computers, with each different computer being at a different communication point of the network.

Each of computers 110, 120, and 130 may include a processor and memory. For example, server 110 may include memory 114 which stores information accessible by a processor 112, computer 120 may include memory 124 which stores information accessible by a processor 122, and computer 130 may include memory 134 which stores information accessible by a processor 132.

The processors 112, 122, 132 may be any conventional processor, such as commercially available CPUs. Alternatively, the processors may be dedicated controllers such as an ASIC, FPGA, or other hardware-based processor. Although shown in FIG. 1 as being within the same block, the processor and memory may actually comprise multiple processors and memories that may or may not be stored within the same physical housing. For example, memories may be a hard drive or other storage media located in a server farm of a network data center. Accordingly, references to a processor, memory, or computer will be understood to include references to a collection of processors, memories, or computers that may or may not operate in parallel.

The memories may include a first part storing applications or instructions 116, 126, 136 that may be executed by the respective processor. The instructions 116, 126, 136 may be any set of instructions to be executed directly (such as machine code) or indirectly (such as scripts) by the processor. In that regard, the terms "applications," "instructions," "steps" and "programs" may be used interchangeably herein.

The memories may also include a second part storing data 118, 128, 138 that may be retrieved, stored or modified in accordance with the respective instructions. The memory may include any type capable of storing information accessible by the processor, such as a hard-drive, memory card, ROM, RAM, DVD, CD-ROM, write-capable, and read-only memories or various combinations of the foregoing, where the applications 116 and data 118 are stored on the same or different types of media.

In addition to a processor, memory and instructions, client computers 120, 130, 131, 133 may have all of the components used in connection with a personal computer. For example, the client computers may include an electronic display 150, 151 (e.g., a monitor having a screen, a touch-screen, a projector, a television, a computer printer or any other electrical device that is operable to display information), one or more user inputs 152, 153 (e.g., a mouse, keyboard, touch screen and/or microphone), speakers 154, 155, and all of the components used for connecting these elements to one another.

Instructions 126, 136 of the first and second client devices 120, 130 may include building applications 125, 135. For example, the building applications may be used by a user to create three-dimensional structures, such as those described further herein. The building applications may be associated with a graphical user interface for displaying on a client device in order to allow the user to utilize the functions of the building applications.

A building application may be a computer-aided design (CAD) three-dimensional (3-D) modeling program or equivalent as known in the art. Available CAD programs capable of generating such a structure include Autodesk® AutoCAD®, Creo® by Parametric Technology Corporation (formerly Pro/Engineer), Siemens PLM Software NX™ (formerly Unigraphics), and CATIA® by Dassault Systèmes. Such structures may be those described in the '421 application.

The data 118, 128, 138 need not be limited by any particular data structure. For example, the data may be stored in computer registers, in a relational database as a table having a plurality of different fields and records, or XML documents. The data may also be formatted into any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data. For example, the data 128 of the first client device 120 may include information used by the building application 125 to create three-dimensional models.

In addition to the operations described above and illustrated in the figures, various other operations will now be described. It should be understood that the following operations do not have to be performed in the precise order described below. Rather, various steps may be handled in a different order or simultaneously. Steps may also be omitted or added unless otherwise stated herein.

An overall three-dimensional representation of a component may first be generated by preparing a CAD model. This overall CAD model may comprise of one or more distinct CAD volumes that are intended to be manufactured as either solid or porous geometries.

Solid CAD volumes can be sliced into layers of a predetermined thickness ready for hatching, re-merging with the porous volume (post-lattice generation) and subsequent manufacture.

Figure 2A:
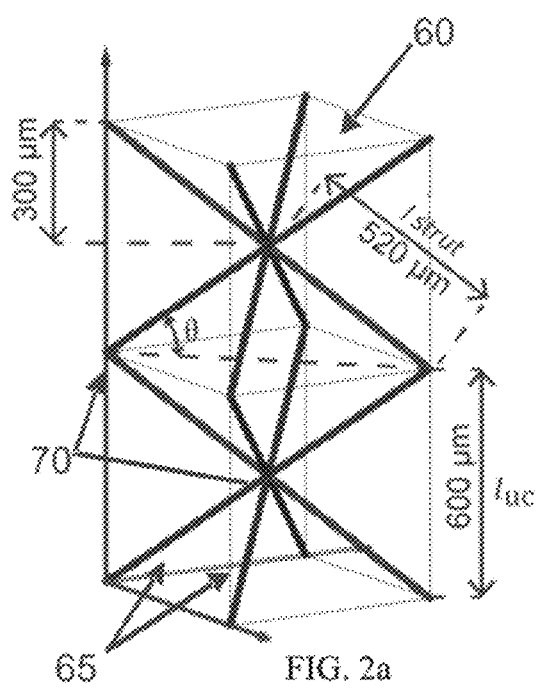
FIG. 2a is a three-dimensional schematic representation of two unit cells and two porous geometries located therein.
Figure 2B:
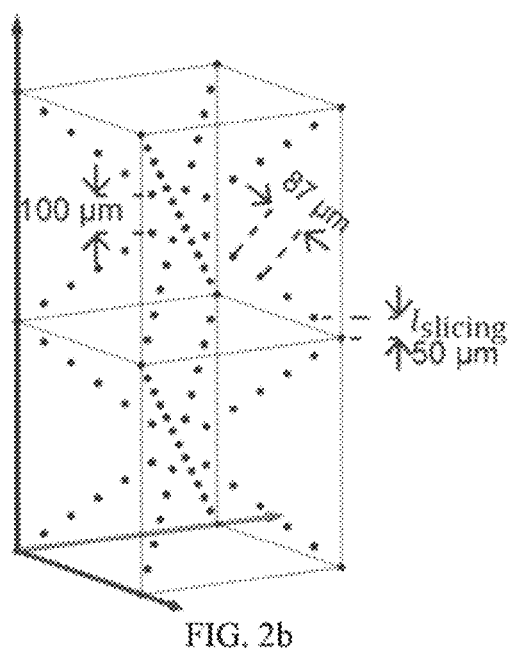

Porous CAD volumes (the basic principles of which are detailed in FIGS. 2a and 2b can be processed using bespoke software. In this case the porous geometry is made up of a plurality of struts organized within tessellating unit cells 60. Many designs of porous geometry are possible to impart various strength, surface, and/or other characteristics into the porous CAD volume. For example, these porous geometries can be used to control the shape, type, degree, density, and size of porosity within the structure. Such porous geometry designs can be dodecahedral, octahedral, tetrahedral (diamond), as well as many other various shapes. In comparison, dodecahedral porous geometries have a different mechanical performance than a tetrahedral structure. Besides these regular geometric shapes, the porous geometries of the present invention may be configured to have irregular shapes where various sides and dimensions have little if any repeating sequences. Porous geometries can even be configured into constructs that closely mimic the structure of trabecular bone. Porous geometries can be space filling, in which all the space within a three-dimensional object is filled with porous geometries but do not always fill the space of an object they are used to produce.

Figure 3:
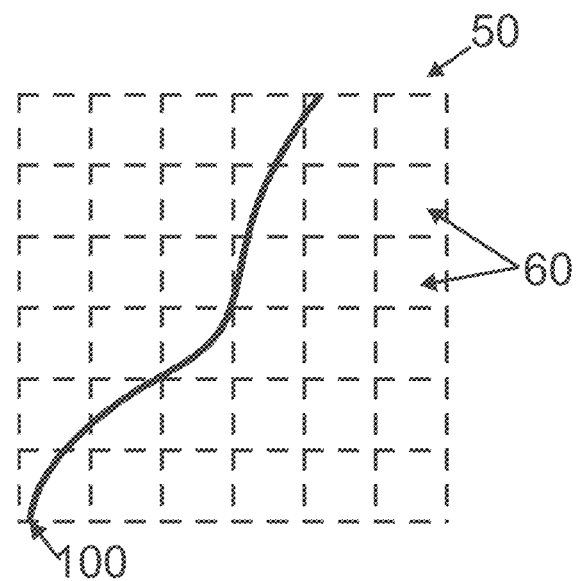
FIG. 3 illustrates a two-dimensional representation of a bounding box containing unit cells in accordance with an embodiment of the invention.

FIG. 3 shows in greater detail a portion of a model build structure 50, generated through the use of an engineering design package such as that described previously herein.

Figure 4:
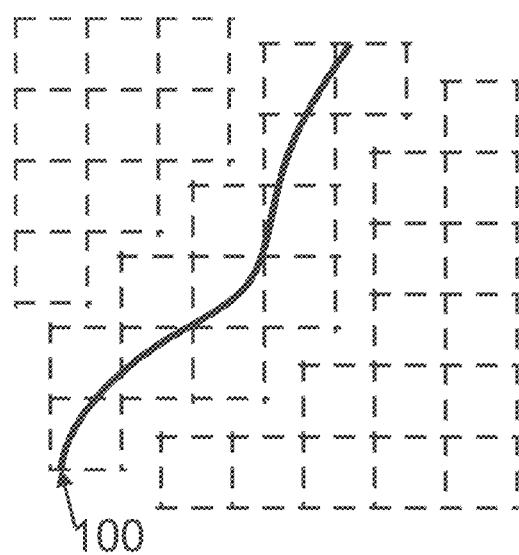
FIG. 4 illustrates the unit cells of FIG. 3 separated into those that intersect a boundary of a porous CAD volume and those that do not intersect the porous CAD volume.
Figure 5:
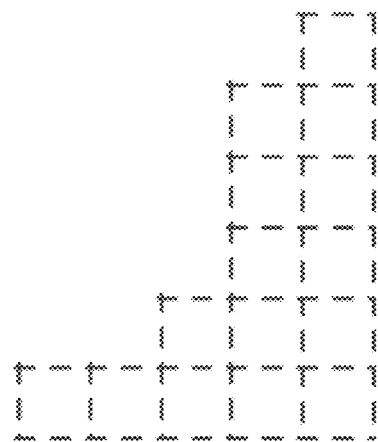
FIG. 5 shows the complete unit cells lying within the boundary of the porous CAD volume that are retained as shown in FIG. 4.
Figure 6:
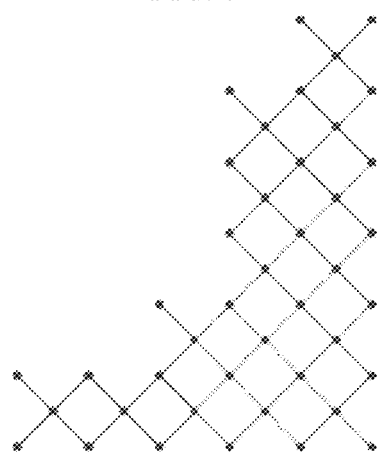
FIG. 6 illustrates a wireframe of porous geometries created within the retained unit cells shown in FIG. 5.
Figure 7A:
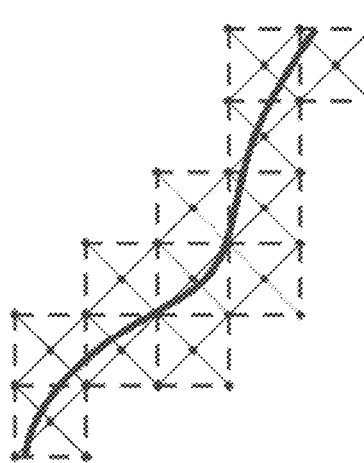
FIG. 7a illustrates a wireframe of porous geometries created within the unit cells that intersect the boundary of the porous CAD volume shown in FIG. 4.

The first step in creating a porous CAD volume is calculate a bounding box, i.e., a box whose x, y, and z dimensions correspond to, or are slightly larger than, a defined boundary of the porous CAD volume, which may be the entire boundary or a portion of a boundary as shown in FIG. 3. This bounding box is then divided into a number of unit cells defined by x, y, and z dimensions. Calculations are then performed during an interrogation on each individual unit cell to ascertain if each cell is within, or intersects the boundary of the porous CAD volume, as illustrated by FIGS. 4 and 5. If these conditions are satisfied for an individual cell, the cell is retained, whereas if they are not, the cell is discarded. Once all cells have been interrogated, porous geometry is populated within the cells that have been retained, as shown in FIGS. 6 and 7a).

Various building blocks make up a porous geometry. Referring again to FIGS. 2a and 3 each of the porous geometries 60 are made up of struts 65, or segments having a length. Nearly all of the struts 65 of the model build structure 50 meet at a node or intersection 70. The position of the nodes may be identified within an array of the data of the processor according to Cartesian, polar coordinates, or other user-defined coordinates.

Figure 7B:
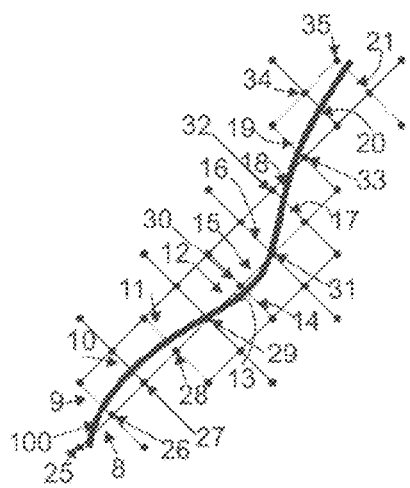

The porous CAD volume has a predefined boundary 100 that corresponds to the intended outer surface of the part being designed. A portion of the boundary 100 is illustrated in FIGS. 7a and 7b. As shown, some of the unit cells 60 along the predefined boundary 100 have overlapping struts 8-21 that cross over the boundary 100. The struts 8-21 have inner nodes 26-29, 31, and 33 within the boundary 100 of the porous CAD volume and outer nodes 25, 30, 32, 34, and 35 outside of the boundary 100.

Figure 8A:
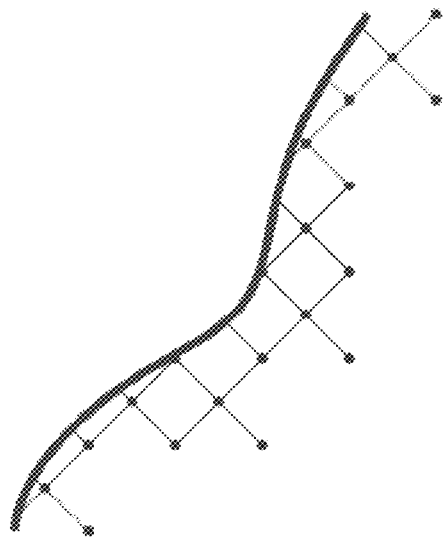
FIGS. 8a and 8b illustrate the wireframe of the porous geometries of FIGS. 7a and 7b after clipping struts of the porous geometries at their intersections with the boundary of the porous CAD volume.
Figure 8B:
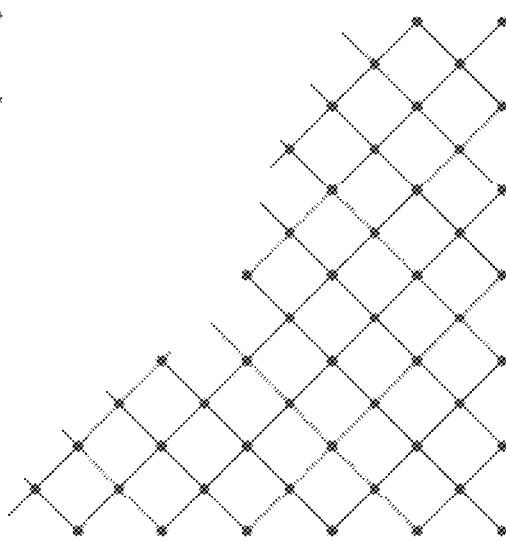

To produce a porous structure having struts that terminate along the boundary, the overlapping struts may be clipped such that any portion of the overlapping struts beyond the predefined boundary is removed. FIG. 8 depicts a model build structure 50 generated according to this clipping approach, in other words, after the overlapping struts 8-21 have been clipped. The overlapping struts 8-21 are now shorter. The ends of each of the overlapping struts 8-21 now lie along the predefined outer boundary 100 and none of the overlapping struts 8-21 extend past the boundary 100.

Figure 19A:
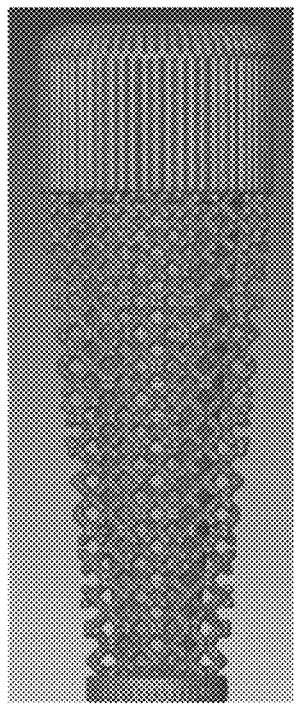
FIGS. 19a-19c illustrate computer-generated models of cylindrical structures created by (a) clipping struts, positioned using Cartesian coordinates, at a boundary of a porous CAD volume, (b) positioning nodes based on polar coordinates, and (c) positioning nodes using Cartesian coordinates including repositioning of the nodes closest to the boundary to positions along the boundary of the porous CAD volume through conformal manipulation.

In some cases this clipping approach may be appropriate. However, the struts that have been shortened may not be supported at their outer points as can be seen in the model of FIG. 19a, and as such they can act as cantilevers and may result in an increased risk of debris formation. In some instances (assuming a flat edge is present), the porous CAD volume may be modified so that the boundary lies along a whole number of unit cells. In this instance there is no need for the clipping operation. This mitigates the possibility of debris generation as the end of each strut is supported by at least one other strut, and is correspondingly less prone to failure.

Figure 9A:
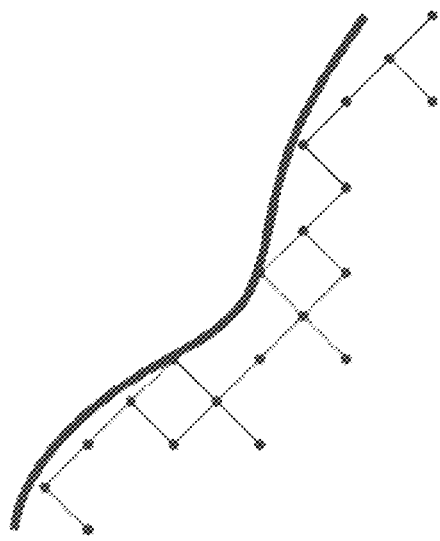
FIGS. 9a and 9b illustrate the wireframe of the porous geometries of FIGS. 7a and 7b after clipping the full lengths of struts that overlap the boundary of the porous CAD volume.
Figure 9B:
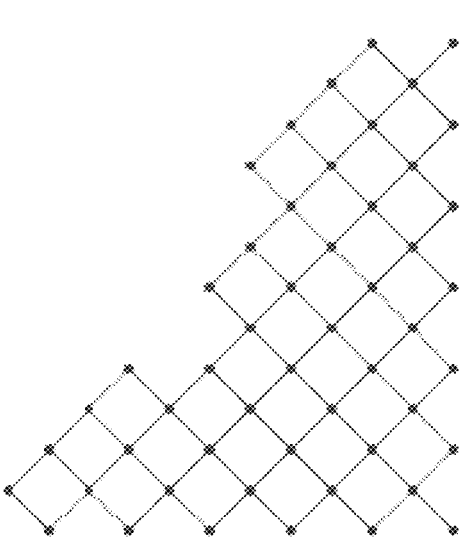

FIGS. 9a and 9b show the model build structure 50 prepared by another approach where the full length of struts that overlap the surface of the porous CAD volume are removed to the inner node. Thus the overlapping struts 8-21 are removed. Preferably, removal of these struts leaves only the complete porous geometries 60. However, this approach may leave the surface rough, uneven and nonconforming to the original porous CAD volume as some of the unit cells 60 do not reach the outer boundary 100.

Figure 10A:
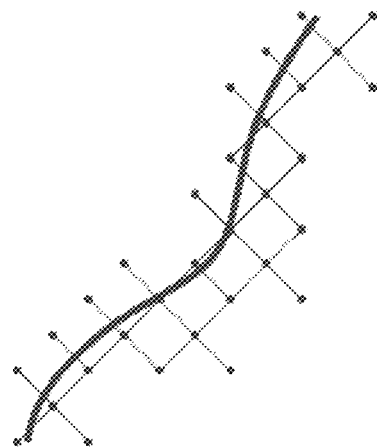
FIGS. 10a and 10b illustrate the wireframe of the porous geometries of FIGS. 7a and 7b after clipping the full lengths of struts that lie entirely outside the boundary of the porous CAD volume.
Figure 10B:
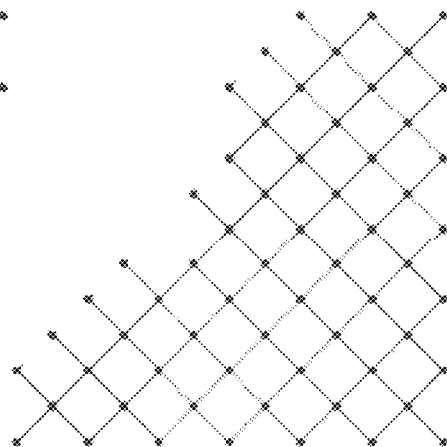

FIGS. 10a and 10b show the model build structure 50 prepared by another approach where the full length of struts that overlap the surface of the porous CAD volume are retained to their respective outer nodes. In this manner, the overlapping struts 8-21 remain beyond the boundary 100 of the porous CAD volume.

Figure 11A:
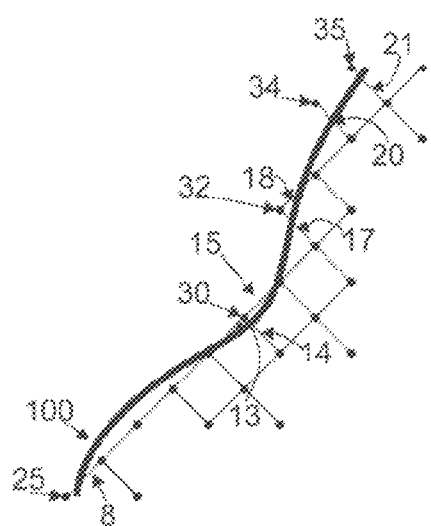
FIGS. 11a and 11b illustrate the wireframe of the porous geometries of FIGS. 7a and 7b after clipping the full length of struts overlapping the boundary and having an inner node closest to the boundary to their respective inner nodes and the full length of struts lying entirely outside the boundary, while retaining the struts having the full length of struts overlapping the boundary and having an outer node closest to the boundary of the porous CAD volume.
Figure 11B:
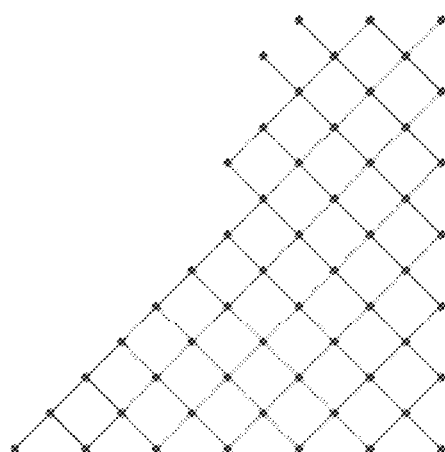

FIGS. 11a and 11b show the model build structure 50 prepared by yet a further approach where each of these struts 8-21 are either fully retained or fully removed, depending on the distance of their nodes from the boundary 100 of the porous CAD volume. In the example shown, each of the unit cells 60 outside the outer boundary 100 as well as the struts 9-12, 16 and 19 are removed (or marked for removal). The struts selected for removal are those overlapping struts in which the node outside the boundary, i.e., the outer node, is further from the boundary than the corresponding node of the overlapping strut inside the boundary, i.e., the inner node. In contrast, the overlapping struts 8, 13-15, 17-18, and 20-21 are not removed because their corresponding nodes 25, 30, 32, 34, and 35, although outside the outer boundary 100 are closer to the boundary 100 than their corresponding inner nodes.

Figure 12A:
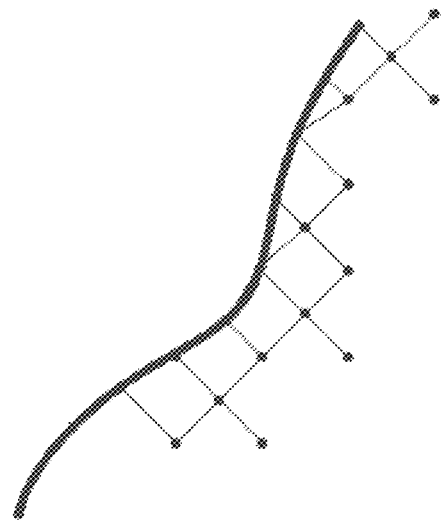
FIGS. 12a and 12b illustrate the wireframe of the porous geometries of FIGS. 11a and 11b, respectively, after repositioning of the nodes closest to the boundary to positions along the boundary of the porous CAD volume through conformal manipulation.
Figure 12B:
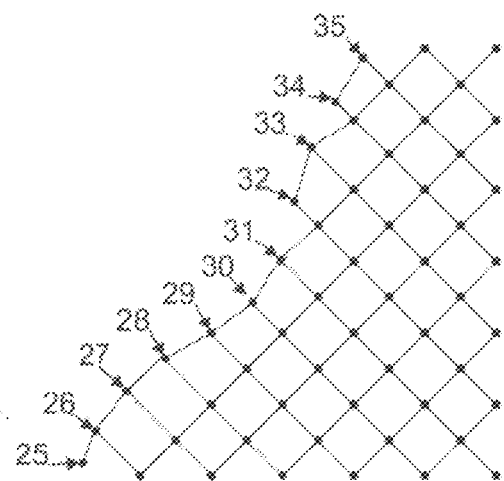

FIGS. 12a and 12b show the model build structure 50 prepared after clipping, followed by the repositioning of the remaining nodes 25-35, closest to the boundary 100 of the porous CAD volume to coincide with the boundary 100. In some embodiments, each of the nodes 25-35 closest to the boundary 100 may be repositioned to a location determined by a mathematical calculation based on the original position of each of these nodes, e.g., the distance from the boundary of each of these nodes, or the original length of the struts attached to these nodes that overlap the boundary or both of these values. In this manner, the shape of the structure may be maintained when having nodes along the boundary.

Figure 19B:
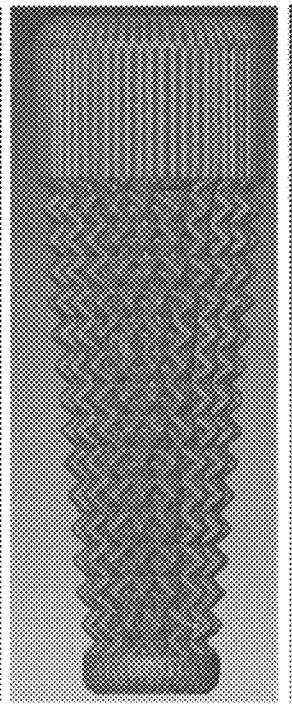
Figure 19C:
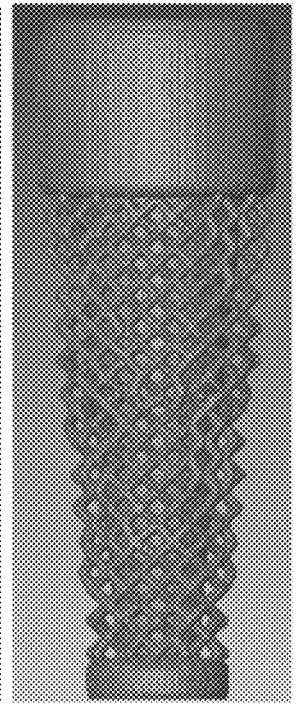
Figure 20A:
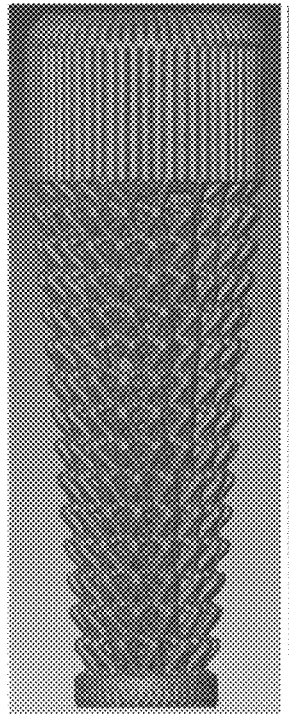
FIGS. 20a-20c illustrate computer-generated models of structures created by positioning struts based on polar coordinates and then displacing nodes by varying amounts to create anti-back out functions.
Figure 20B:
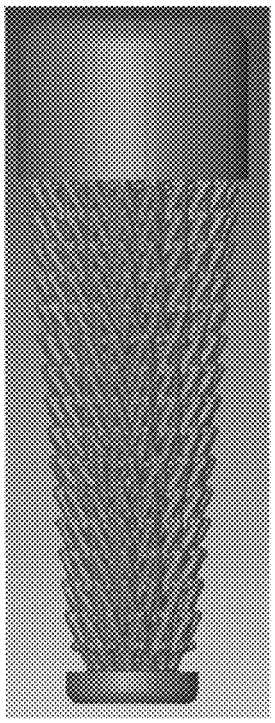
Figure 20C:
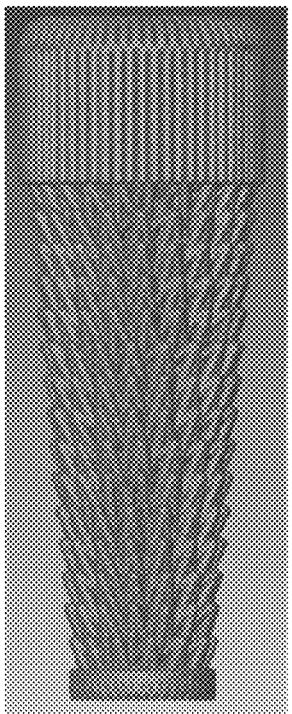

As further shown in FIGS. 12a and 12b, when the nodes 25-35 are repositioned, the remaining struts connected to the nodes 25-35 may then be lengthened or shortened as required to maintain connectivity between the nodes. In this manner, the outermost nodes and struts may be positioned such that they do not coincide with the boundary by any function of the cell size or geometry. This effect can be seen clearly in FIG. 19c.

In a variant of this embodiment, the nodes 25-35 may not be moved but instead discarded and replaced by new nodes. Additionally, the struts connected to the nodes 25-35 may be replaced by new struts that are longer or shorter than the original struts to maintain the connectivity between the nodes.

The use of polar or spherical coordinates to define nodes may be preferred to the use of Cartesian coordinates when a surface of a model build structure to be formed is curvate or cylindrical. In this manner, nodes repositioned on a boundary may be positioned at the same angle defining a replaced node but at a different radius from the origin of a polar coordinate system being used to create a model build structure. However, other user-defined coordinates may be used to create conformal structures. In other words, a user-defined node positioning system may be used to form a model build structure having nodes along an outer boundary that fit the contours of the outer boundary of the component being modeled.

Figure 13A:
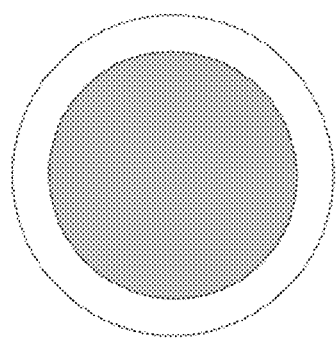
FIGS. 13a and 13b show plan and side cross-sectional views, respectively, of a solid CAD volume surrounded by a boundary of a porous CAD volume of a tapered cylindrical geometry for use in accordance with an embodiment of the invention.
Figure 13B:
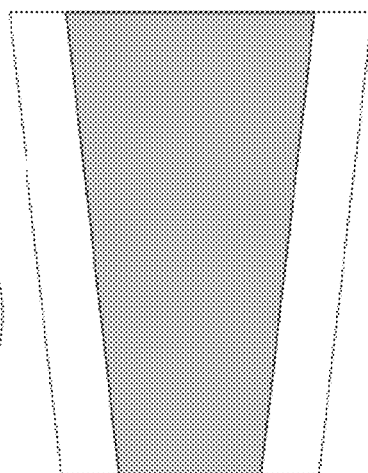

FIGS. 13a and 13b show various cross sections of a tapered, cylindrical geometry. The gray color represents the solid CAD volume which is bounded by a clear, porous CAD volume.

FIGS. 14a and 14b further show the geometry of FIGS. 13a and 13b subsequent to the generation of a plurality of outer nodes 410 and a plurality of inner nodes 430 along inner and outer boundaries 435, 445 of the porous CAD volume. Such nodes define the vertices of unit cells 450 which are created by virtually slicing the porous CAD volume according to the unit cell height. This operation produces polar rings that are then populated with volumes that pattern radially around the ring of the part. These volumes define the unit cells for the part.

FIGS. 15a-15c show the population of the unit cells 450 created in the previous stage. The depicted geometry is based on the preferred octahedral cell as described previously herein but could be based on any porous geometry. These porous geometries are then defined by nodes with connecting struts or segments 480, all of which meet at the defined surface of the porous CAD volume 500. This effect can be seen clearly in FIG. 19b.

Figures 16A, 16B:
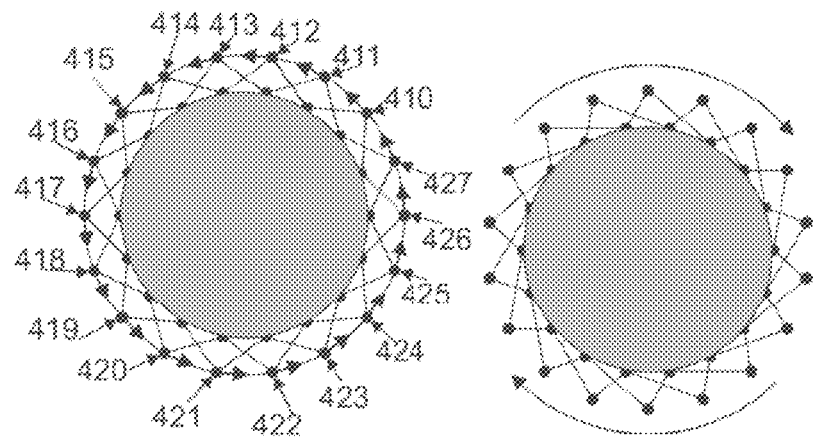
FIGS. 16a and 16b illustrate plan cross-sectional views of the tapered cylindrical geometry of FIGS. 15a-15c, before and after, respectively, repositioning of the nodes circumferentially about the cylindrical geometry at a boundary thereof in the same direction to create a structure with torque resistant properties.
Figure 17:
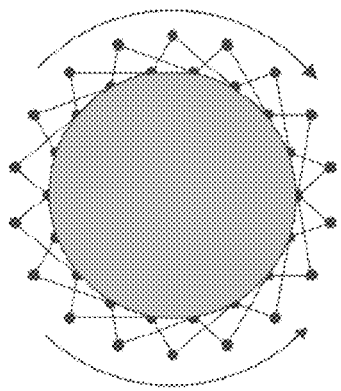
FIG. 17 illustrates a plan cross-sectional view of the tapered cylindrical geometry of FIG. 16a after repositioning of the nodes circumferentially about the cylindrical geometry at the boundary thereof in opposite directions on opposite portions to create a structure with torque resistant properties.

Creation of beneficial surface properties can be achieved through the movement of the nodes 410 at the outer surface 500 of the porous CAD volume. FIGS. 16a, 16b, and 17 detail the creation of torque or movement resisting features on the surface of cylindrical components. The nodes 410-427 that lie on the outermost boundary of the porous CAD volume 500 can be manipulated to be repositioned along the surface of the porous CAD volume 500 in either direction to create a deformed unit cell with a preferential direction of movement. Such manipulation involves the changing of the coordinate positions of the nodes. For example, the angular component of at least some of the polar coordinates of the nodes along the boundary may be modified in the same or opposite directions to produce an anti-torque effect. In another example, the height component and in some instances the radius component as well of the nodes along the boundary may be modified in the same or opposite directions to produce an anti-backout effect. In producing either of these effects, the struts may correspondingly be lengthened or shortened as necessary to maintain connectivity with the nodes along the boundary. The amount that any coordinate is changed can be based on any empirical or mathematical function.

Figures 18A, 18B:
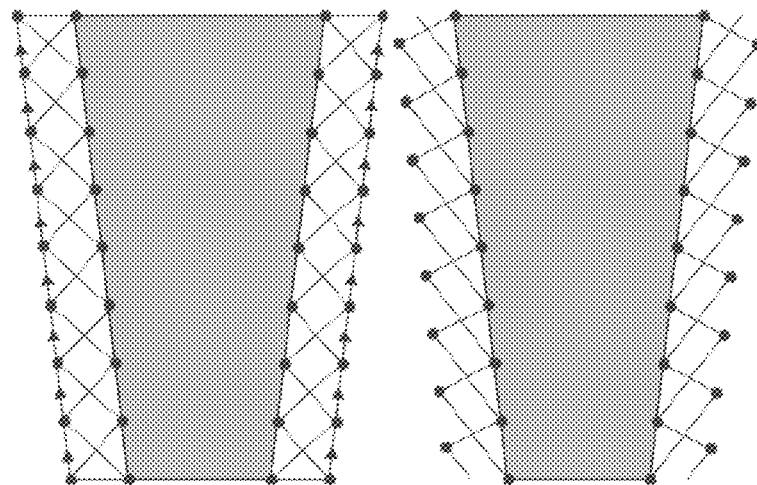
FIGS. 18a and 18b illustrate side cross-sectional views of the tapered cylindrical geometry of FIGS. 15a-15c, before and after, respectively, repositioning of the nodes longitudinally along the cylindrical geometry at the boundary thereof to create structures with anti back-out properties.

A similar modification in the vertical direction is shown in FIGS. 18a and 18b. In this case the nodes on the outermost boundary of the porous CAD volume 500 are manipulated to be repositioned in the vertical direction to create features that are resistant to the part being extracted after insertion.

Figure 21:
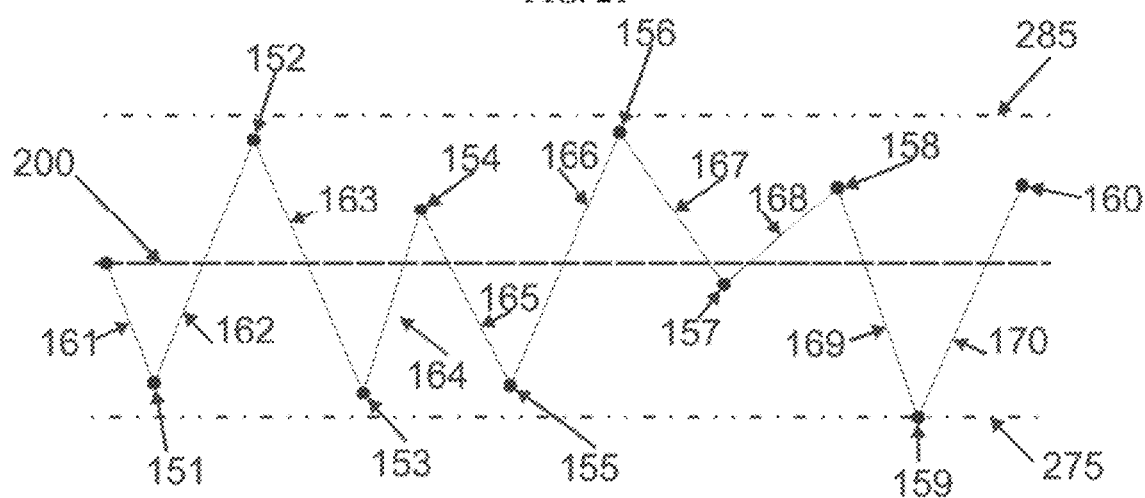
FIG. 21 is a schematic of a surface produced by manipulating nodes in accordance with an embodiment of the invention to create a desired surface roughness.

In another example, as illustrated in FIG. 21, surface features can be generated on any part where the surface is made up of connected nodes. Intrinsic surface properties can be created through the movement of nodes away from the surface to positions both inside and outside of the porous CAD volume. The location of the new position of a node 151-160 and corresponding struts 161-170 may be a parameter of the building application such that the repositioned node 151-160 will be at a position selected to satisfy a predetermined theoretical surface roughness along the pre-defined portion of the outer boundary 200. The theoretical surface roughness may be defined by a formula for surface roughness, such as any of the ANSI/ASME B46.1-2009 standards for surface roughness $R_a$, $R_s$, $R_z$, or $R_q$. In addition, the new positions of a group of nodes 151-160 and corresponding struts 161-170 along a predefined portion of the outer boundary 200 may be selected such that the surface roughness of the predefined portion of the outer boundary 200 is a predetermined value. Thus, the positions chosen may be selected at random so long as the aggregate of the positions of the nodes 151-160 and corresponding struts 161-170 satisfy the theoretical surface roughness chosen. For example, if $R_z$ is the parameter, then each of the struts 161-170 and nodes 151-160 along the outer boundary 200 must fall within a set distribution between minimum and maximum heights 275 and 285, respectively, as shown in FIG. 21.

Figure 23A:
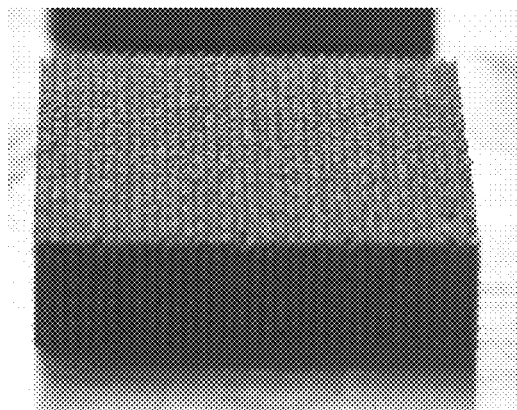
FIGS. 23a and 23b show coupons having surfaces prepared by (a) applying and (b) not applying a predetermined surface roughness thereto in accordance with an embodiment of the present invention.
Figure 23B:
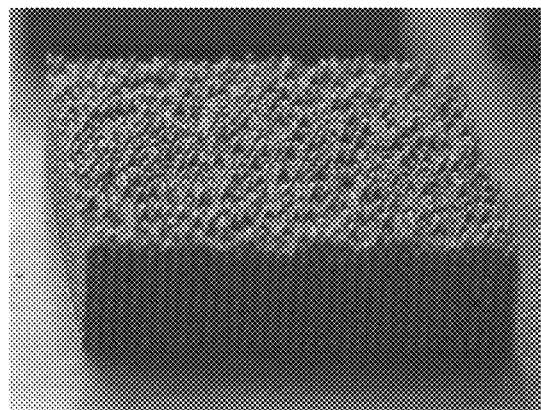

FIGS. 23a and 23b depict the surfaces of flat structures formed using a conventional modeling method and some of the approaches described herein. FIG. 23a is a photograph of a coupon formed by selective laser melting of powdered metal prepared in accordance with a method known in the prior art. To produce the coupon, a model build structure was prepared with the upper nodes of the regular, octahedral, porous geometry deliberately intersecting the upper surface boundary of the cuboid porous CAD volume.

FIG. 23b is a photograph of another coupon formed using the same selective laser melting process as the coupon in FIG. 23a. The model build structure used to produce the coupon in FIG. 23b used the same lattice structure as the coupon in FIG. 23a. However, an approach in accordance with those described herein was employed to produce the top surface of the model build structure corresponding to the roughened top surface 200 shown in FIG. 23b. An algorithm was applied to the nodes at the upper surface of the porous CAD volume. This algorithm required a predetermined surface roughness (to a corresponding $R_a$, $S_a$ or other standard roughness measure) as described previously. FIG. 23b shows the resultant built geometry illustrating the surface roughness obtained.

Figure 22A:
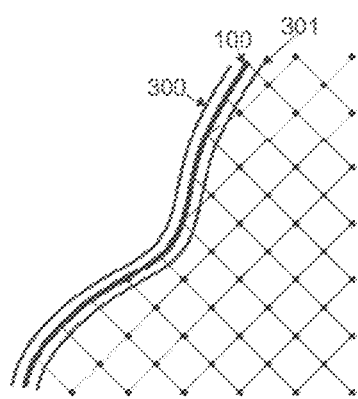
FIGS. 22a-22c illustrate a process of roughening a predetermined surface by moving nodes within a defined region along the surface in accordance with an embodiment of the invention.
Figure 22B:
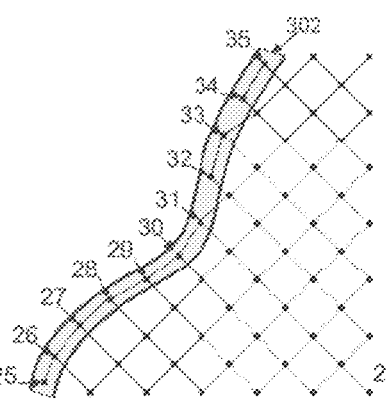
Figure 22C:
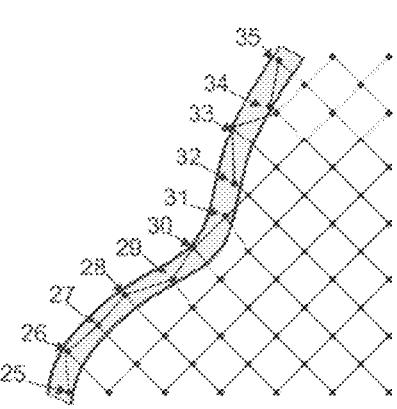
Figure 24:
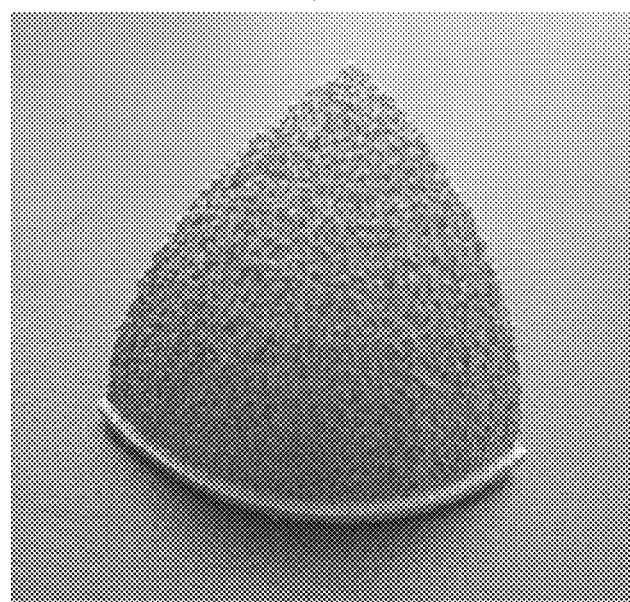
FIG. 24 shows a curved surface prepared by applying a predetermined surface roughness thereto in accordance with an embodiment of the present invention.

The features previously described herein can be used on any surface. An example of their use on curved surfaces is shown in FIGS. 22a-22c. A porous CAD volume that conforms to a surface 100 is used as the base. An upper bound 300 and lower bound 301 define a region 302 in which the surface nodes 25-35 can be repositioned. As in the example shown in FIGS. 8a and 8b, the amplitude and direction of each movement can be controlled to create any predetermined theoretical surface quality e.g., roughness or surface marking. This same algorithm has been applied to a curved surface detailed in FIG. 24 where the nodes have been moved by a set amplitude to get a desired roughness value on a curved surface.

Figure 25A:
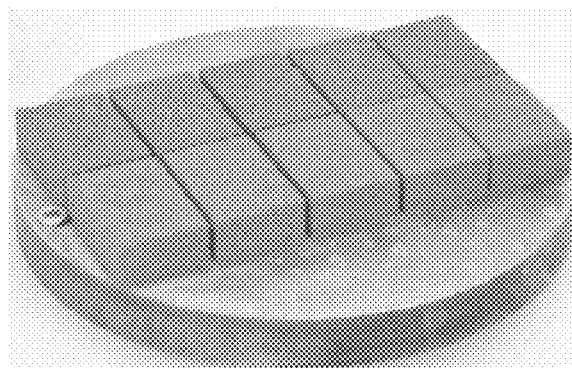
FIGS. 25a and 25b show examples of flat surfaces prepared by applying a predetermined surface roughness thereto to create surface labelling in accordance with an embodiment of the invention.
Figure 25B:
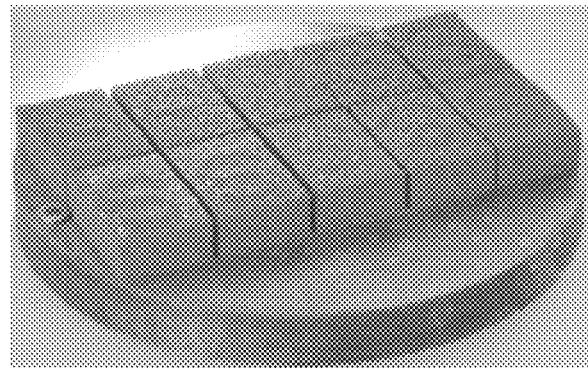

Specific use can be made of these different roughening algorithms to produce desired effects, for example surface marking for use in product identification. This can be seen in FIGS. 25a and 25b which illustrates that it is possible to produce markings that are invisible under normal light, and visible under angular directed light, for example by creating areas of different roughness, which may be sub-flush or proud of the surface. This could also be applied in the form of a 2-D barcode or QR code that may contain proprietary information relating to the specific implant to which the coding has been applied. In this manner, the marking may be readable by hand-held laser scanners or other well-known devices.

Figure 26A:
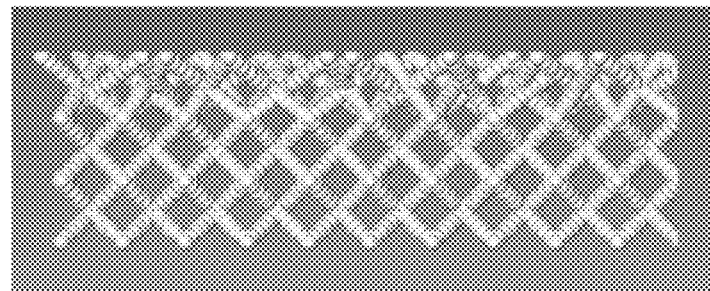
FIGS. 26a and 26b illustrate side elevation and plan views, respectively, of a model of a flat surface having surface node deformation to create irregularity in a specific area of a regular structure in accordance with an embodiment of the present invention.
Figure 26B:
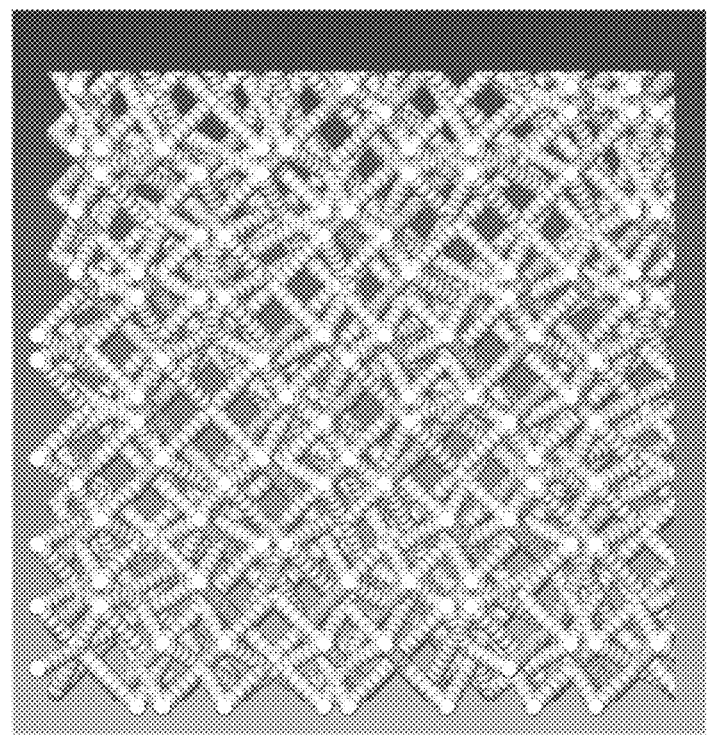
Figure 27:
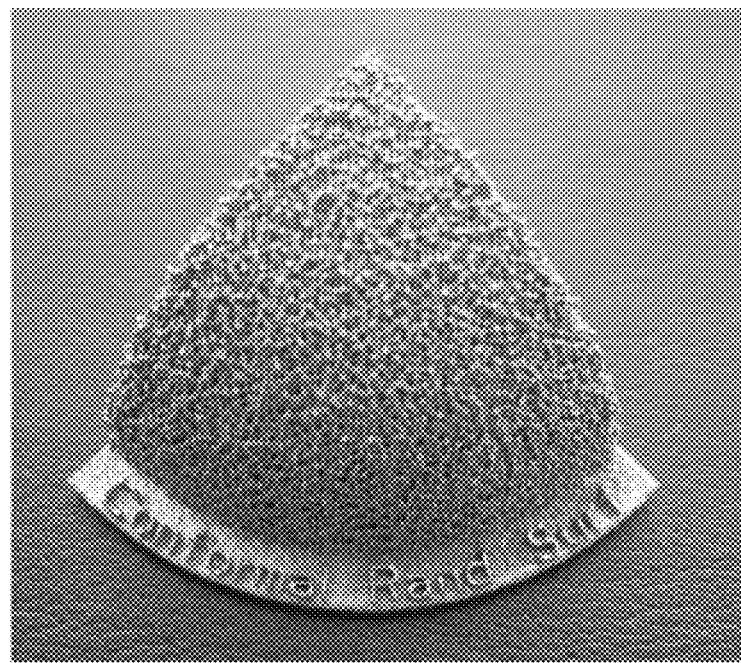
FIG. 27 shows an example of a curved surface having surface node deformation to create irregularity in a specific area of a regular structure in accordance with an embodiment of the invention.

Another application of the movement of the nodes along and through the surface is demonstrated in FIGS. 26a and 26b. These relate to the creation of an irregular appearance at the surface of a regular structure. The nodes that are at the surface can be moved along, out of, into or in any combination of these movements to create a modified surface that has irregular qualities but which is based on a regular structure.

Figure 28A:
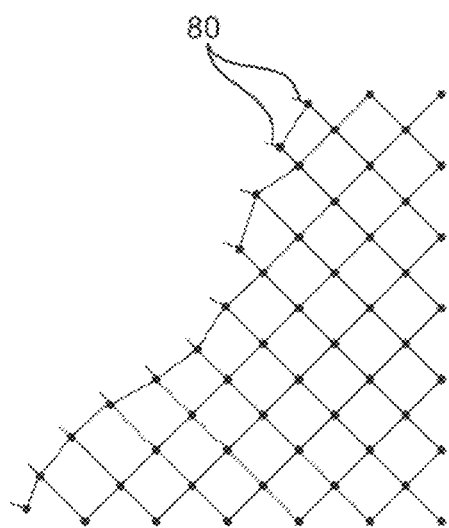
FIGS. 28a and 28b illustrate the wireframes of the porous geometries of FIGS. 12b and 15a-15c, respectively, having portions of struts added to the surface nodes of the respective porous CAD volumes.
Figure 28B:
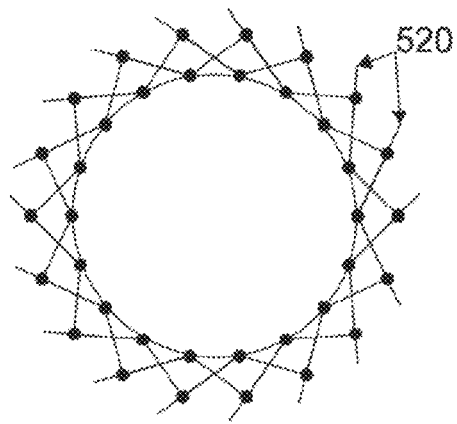

Yet a further method of creating surface roughness is shown in FIGS. 28a and 28b. Additional struts 80 may be added onto the outer nodes 25-35 as defined in the arrangement shown in FIG. 12b, and additional struts 520 may be added onto outer nodes 410-427 as defined in the arrangement of FIG. 15a-15c. These additional struts do not connect to another strut. In this manner, these struts may give rise to a resistance to movement in a direction at an angle sufficiently perpendicular to the surface.

Figure 33A:
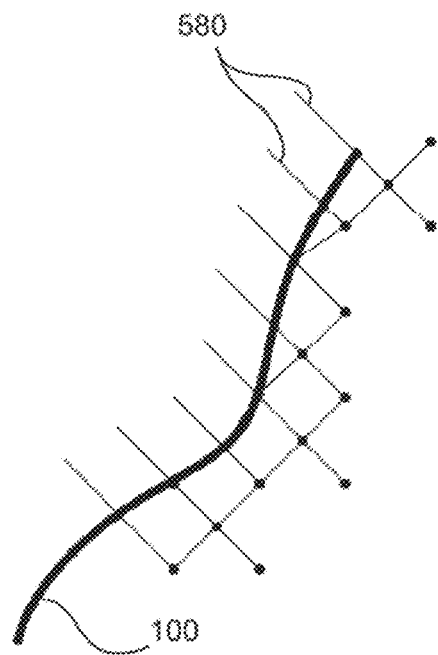
FIGS. 33a and 33b illustrate elongated fixation elements extending from the wireframe of FIGS. 12a and 12b, respectively, in accordance with an embodiment of the invention.
Figure 33B:
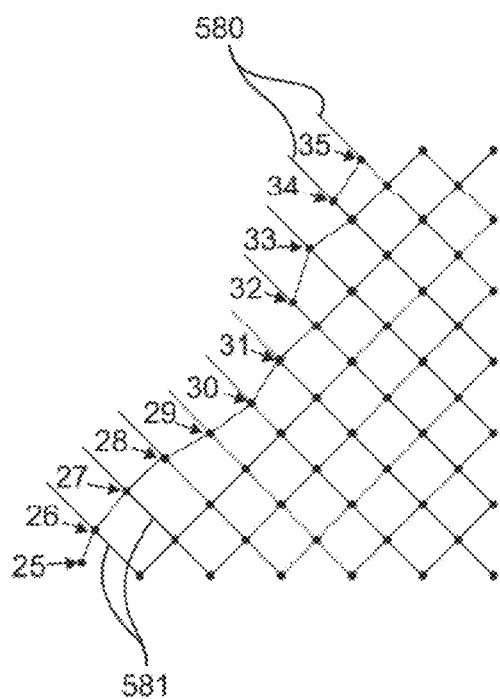

As contemplated by an embodiment of this invention, self-retaining features, such as the additional struts 520, may be used to produce a "VELCRO" type effect in tangible structures formed from a corresponding model build structure. In this manner, the outside surface of one tangible structure having a self-retaining feature may be an inverse representation of the outside surface of a mating tangible structure having a corresponding self-retaining feature. For example, the mating structures may each have additional struts that interlock or engage with one another. In other embodiments, additional struts of one structure may fit into pores or holes on the surface of another structure in a "hook and eye" formation or through an interference fit to attach the two structures. As shown in FIGS. 33a and 33b, elongated fixation elements 580 may be substantially parallel to each other and extend from the outer nodes 25-35. In the example shown, the fixation elements 580 are additional struts incorporated into the model build structure that are only connected to the model build structure at one node in which the other end of the fixation elements lies outside the boundary 100.

The fixation elements 580 may correspond to "microspikes" of an intended physical structure that are created using the model of the elements 580. The microspikes may mesh in an interference fit with another mating structure which may have receiving holes for the microspikes or which may be soft enough to permit the microspikes to puncture through a surface of the structure. For instance, the microspikes preferably may be capable of piercing through a bone surface, in particular a spongy bone surface. The elements 580 may extend in a predetermined direction relative to the boundary 100. When used in this manner, at least a portion of the fixation elements 580 preferably may be substantially parallel to each other such that the portion of the substantially parallel fixation elements has a density within a plane perpendicular to the fixation elements 580 of approximately 20 to 400 elements per square centimeter, and more preferably approximately 50 to 200 elements per square centimeter. Such densities may provide sufficient surface contact between the physical porous structure corresponding to the porous CAD volume and a mating structure in which the fixation elements may be inserted to maintain an interlock between the physical and mating structures. When a portion of the fixation elements 580 are substantially parallel to each other, the fixation elements 580 also may preferably be spaced a distance from each other that is larger than the largest pore diameter of the bone.

The fixation elements 580 may extend in a number of predetermined directions relative to the boundary. In some arrangements, the fixation elements 580 may be perpendicular to the boundary 100. As shown in the example of FIGS. 33a and 33b, the elements 580 may extend, in some instances, in a direction that is different from the direction of struts 581 that intersect with struts forming the boundary of the porous CAD volume. The fixation elements 580 preferably may form an angle of 10° to 90°, and more preferably may form an angle of 30° to 90°, with the boundary 100. Typically, the predetermined direction of fixation elements 580 intended to be mated with a structure will be substantially parallel to the direction of a seating area of a mating structure into which the fixation elements 580 are adapted to be received.

Figure 34A:
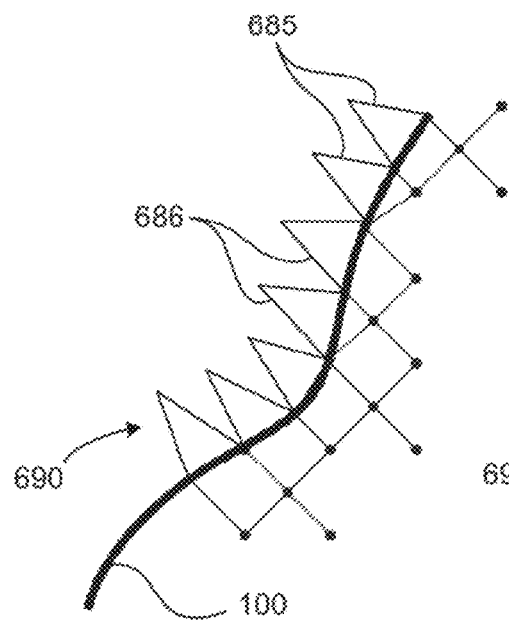
FIGS. 34a and 34b illustrate elongated fixation elements extending from the wireframe of FIGS. 12a and 12b, respectively, in accordance with an embodiment of the invention.
Figure 34B:
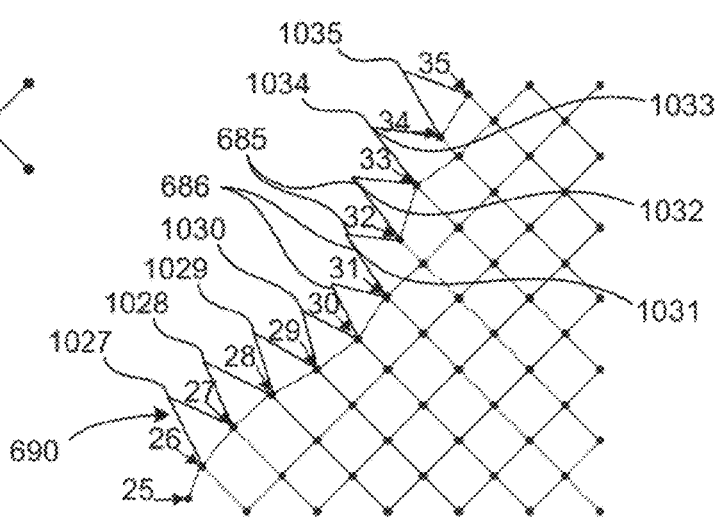

In accordance with another embodiment, with specific reference to FIGS. 34a and 34b, adjacent struts 685, 686 may be attached to the porous CAD volume, extending from the outer nodes 25-35 on one end and be attached to each other on the other end at nodes 1027-1035 to form portions of a plurality of elongated fixation elements 690. For example, strut 685 may extend from node 335 on one end to node 1035 on the other end. Likewise, strut 686 may extend from node 34 on one end to node 1035 on the other end. Similarly, other adjacent struts 685, 686 along the boundary 100 may extend from the porous CAD volume and connect to each other.

It should be noted that FIGS. 33a and 33b and FIGS. 34a and 34b only illustrate a two-dimensional slice of a portion of the porous CAD volume. Accordingly, in the example of FIG. 34, two or more other struts (not shown) may be connected to both strut 685 and strut 686 to form other sides of a fully connected porous geometry (e.g., formed using a tetrahedron unit cell as described previously herein) that form the elongated fixation element 690. The fixation element 690 may be more space-filling, but may also provide greater bending and torsional strength than the fixation elements 580 shown in FIG. 33. These space-filling fixation elements may also provide for interference fits with mating structures. Due to their greater surface area for contacting a mating structure, these fixation elements may also provide for greater adhesion to a mating structure than fixation elements, such as elongated fixation elements 580.

As in the example shown in FIGS. 34a and 34b, the fixation elements 690 may have a longitudinal axis extending between each of the connected struts extending from the porous CAD volume. Moreover, as in the arrangement shown, the longitudinal axes of the fixation elements 690 may be substantially parallel to each other along at least a portion of the boundary 100. In such a configuration, the fixation elements 690 preferably may have a density within a plane perpendicular to the longitudinal axes through the fixation elements 690 of approximately 20 to 500 elements per square centimeter, and more preferably approximately 50 to 300 elements per square centimeter.

In the views shown in FIGS. 35*a*-35*c*, elongated fixation elements 790 are formed by struts 785 and 786 and two other struts (not shown) in a manner similar to that described for the fixation elements 690. In contrast with the fixation elements 690, however, the fixation elements 790 extend from a solid CAD volume 795. In this manner, the fixation elements 790 extend from nodes 791 formed at the interface of the solid CAD volume 795 and a porous CAD volume 780. Moreover, in the arrangement shown, fixation elements 790 are formed such that a longitudinal axis through the fixation elements is perpendicular to a plane tangential to the solid CAD volume 795 at an imaginary point of intersection between the longitudinal axis and the solid CAD volume 795. Accordingly, when used in the tapered cylindrical geometry shown in the views of FIGS. 35*a* through 35*c*, the elongated fixation elements 790 extend from the solid CAD volume 795 such that the longitudinal axes of fixation elements 790 within a given plane around the circumference of the model build structure are not parallel.

As shown in FIG. 36, a model build structure of a femoral knee implant 1100 may be formed in the manner described previously herein such that a porous CAD volume 1180 is mated to a solid CAD volume 1195 at an interface 1185. As shown, elongated fixation elements, such as the fixation elements 1191, 1192 may extend from the porous CAD volume 1180 such that the longitudinal axes through at least some of the elongated fixation elements is not parallel. In this manner, the fixation elements may be used to create microspikes of the intended implant that correspond to the fixation elements which resist movement of the implant in multiple directions to secure the implant against a patient's femur. In alternative arrangements, the fixation elements may extend from the solid CAD volume 1195 at the interface 1185 in a manner similar to the extension of the fixation elements 790 shown in FIGS. 35*a*-35*c*. In the example of FIG. 36, the fixation elements may be portions of fully connected porous geometries, such as those shown in FIGS. 34*a* and 35*b* and FIGS. 35*a*-35*c*, although other shapes of fixation elements may be used such as single struts, like those shown in FIG. 33.

Figure 37A:
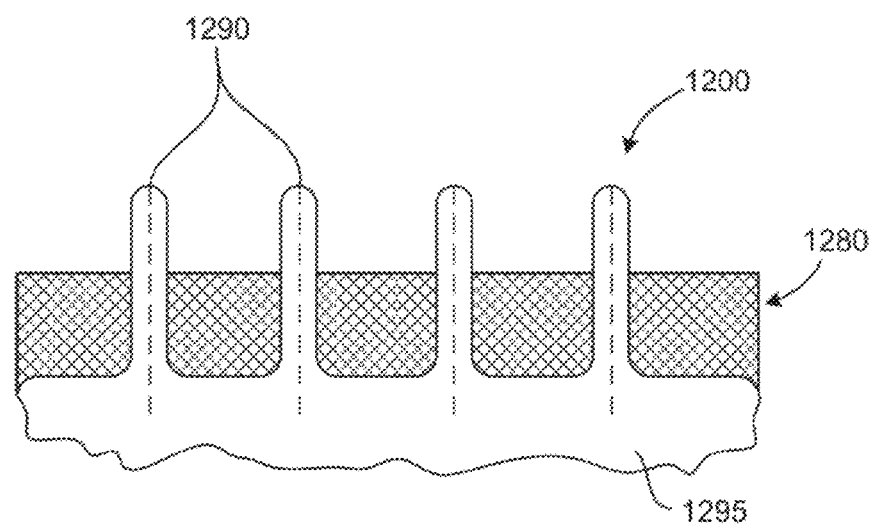
FIGS. 37a and 37b show a portion of a model build structure of a tibial knee implant having elongated fixation elements extending from a solid CAD volume thereof and through a porous CAD volume thereof in accordance with an embodiment of the invention.
Figure 37B:
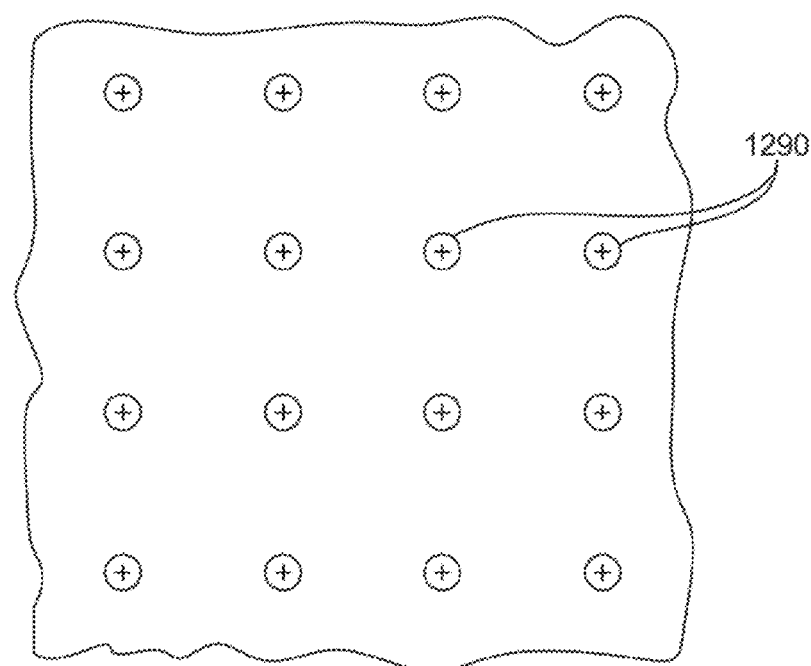

As is shown by the portion of a model build structure used for a tray of a tibial knee implant 1200 in FIGS. 37*a* and 37*b*, fixation elements 1290 may be formed to extend from a solid geometry 1295. In this manner, when an intended physical structure is formed using a rapid prototyping process as described further herein, the fixation elements 790 may be built, such as through powder metal processes, directly onto a substrate. Furthermore, the fixation elements 1290 may additionally be formed such that they extend through a porous CAD geometry 1280. In this manner, a porous ingrowth structure (corresponding to and built using the porous CAD geometry 1280) may provide structural support along a portion of microspikes (corresponding to and built using the fixation elements 1290) during sideloading against the microspikes.

Still other formations along the surface of the porous CAD volume include a barbed geometry with corresponding ends, a hooked geometry with corresponding ends, deformable loops, or variations in the depth of the roughening applied to mating surfaces as described previously herein, to create an interlock between the mating surfaces. In some instances, these types of positive engagement may remove or minimize the need for mechanical fixation devices such as bone screws or other assembly devices.

Other variations of the fixation elements and corresponding microspikes also may be used. The microspikes may be formed using other shapes of unit cells, e.g., octahedral, dodecahedral, etc. The fixation elements and corresponding microspikes may have various shapes and sizes in comparison to other structures having these features. Moreover, various shapes and sizes of fixation elements and microspikes may be used at different portions of the surface of a corresponding CAD geometry or corresponding intended physical structure, respectively. Furthermore, the microspikes and corresponding fixation elements may or may not be used in conjunction with additional engineering structures and respective models thereof, such as keels, pegs, stems, and spikes, for additional device stabilization. Such engineering structures may be integral, i.e., form part of a monolithic structure, with or may be separately added or fixed to, e.g., by fasteners, to intended physical structures. When used in conjunction with additional engineering structures, the fixation elements and corresponding microspikes may extend from the additional engineering structures themselves as well as from other portions of the respective model build structure and intended physical structure. Although the formation and use of fixation elements (and corresponding microspikes) have been described with respect to a femoral and tibial knee implants, such features may be used in the production of other prosthetic devices such as acetabular, patella, shoulder glenoid, finger, and ankle implants, or the like.

Figure 29:
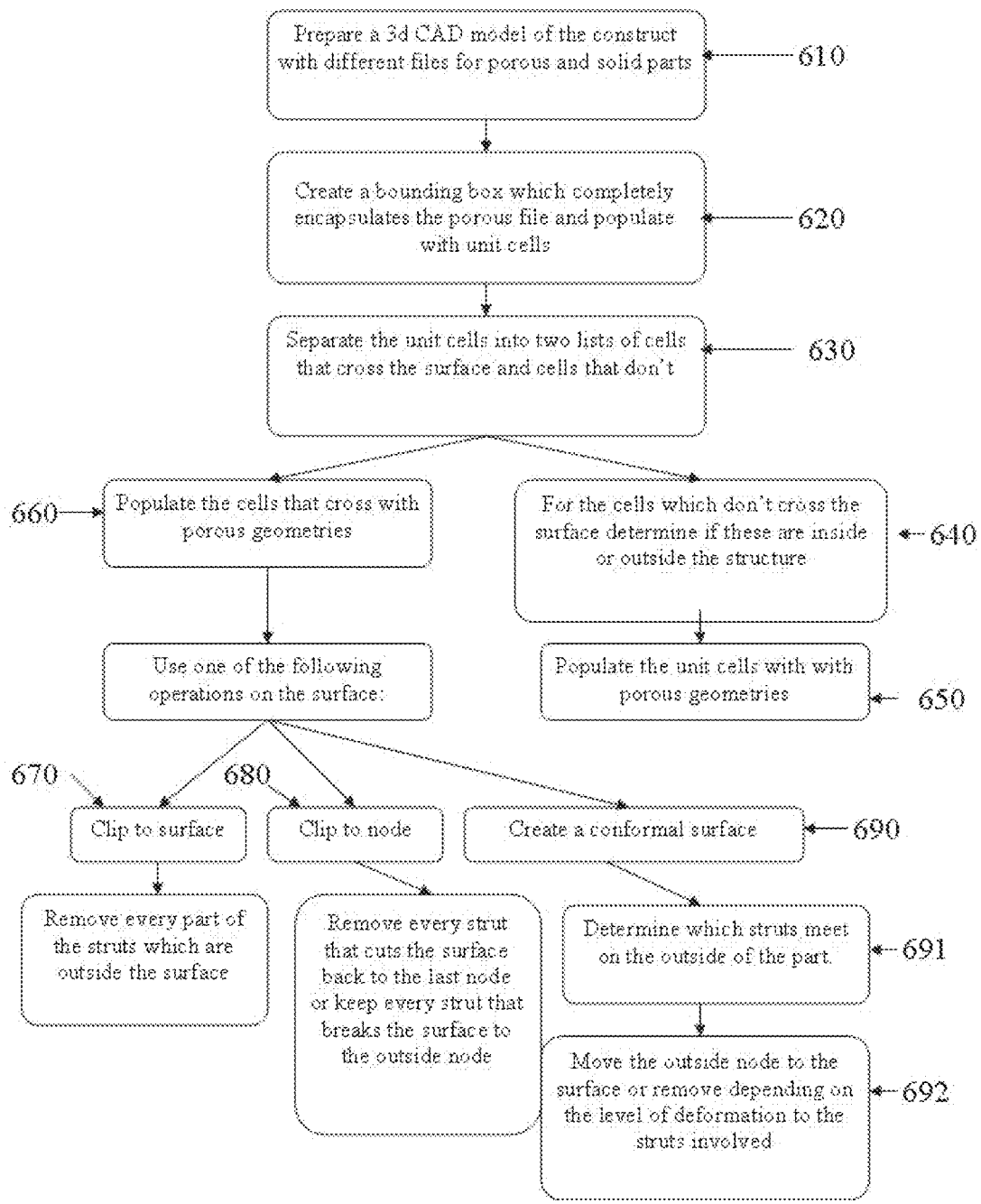
FIG. 29 is a process flow diagram in accordance with an embodiment of the invention.

A flow diagram shown in FIG. 29 details an embodiment of the creation of porous geometries within a Cartesian coordinate defined unit cell. At block 610, a computer-generated model of a three-dimensional structure is prepared. A bounding box is created by a processor. This bounding box is populated with unit cells 620.

The spatial interaction of the unit cells with the surface of the porous CAD volume is determined, by a processor, and two pathways are created at a step 630. The unit cells that do not make contact with the surface are then interrogated to determine their position at a step 640. Unit cells that lie outside the structure are discarded. Unit cells that are within the porous CAD volume are populated with porous geometries 650.

The unit cells that cross the surface of the porous CAD volume are populated with porous geometries. The struts of porous geometries can then either be clipped to the surface at a step 670 or clipped to a node at a step 680 as described previously herein. In other words, the struts may be clipped to an inner node, an outer node, or at the boundary of the porous CAD volume. However, this approach may leave the surface rough, uneven, and nonconforming to the original porous CAD volume.

Through steps 690-692, the nodes at the surface can also be manipulated so that all the surface nodes lie on the outer boundary of the porous CAD volume to create a conformal surface.

Figure 30:
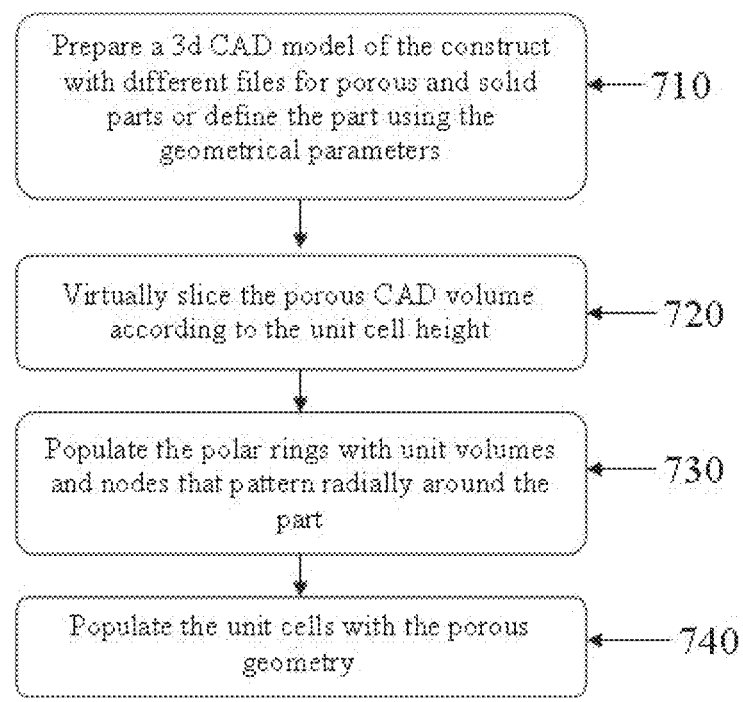
FIG. 30 is another process flow diagram in accordance with an embodiment of the invention.

A process flow diagram shown in FIG. 30 details an embodiment of the creation of porous geometries within polar or cylindrical coordinate defined unit cells. At a step 710, a computer-generated model of a three-dimensional structure is prepared or a part is defined using geometric parameters.

This model may then be sliced virtually at a step 720 to produce polar rings that can then be populated with unit cells and nodes in a radial pattern at a step 730. These unit cells may be populated with porous geometries at a step 740.

Figure 31:
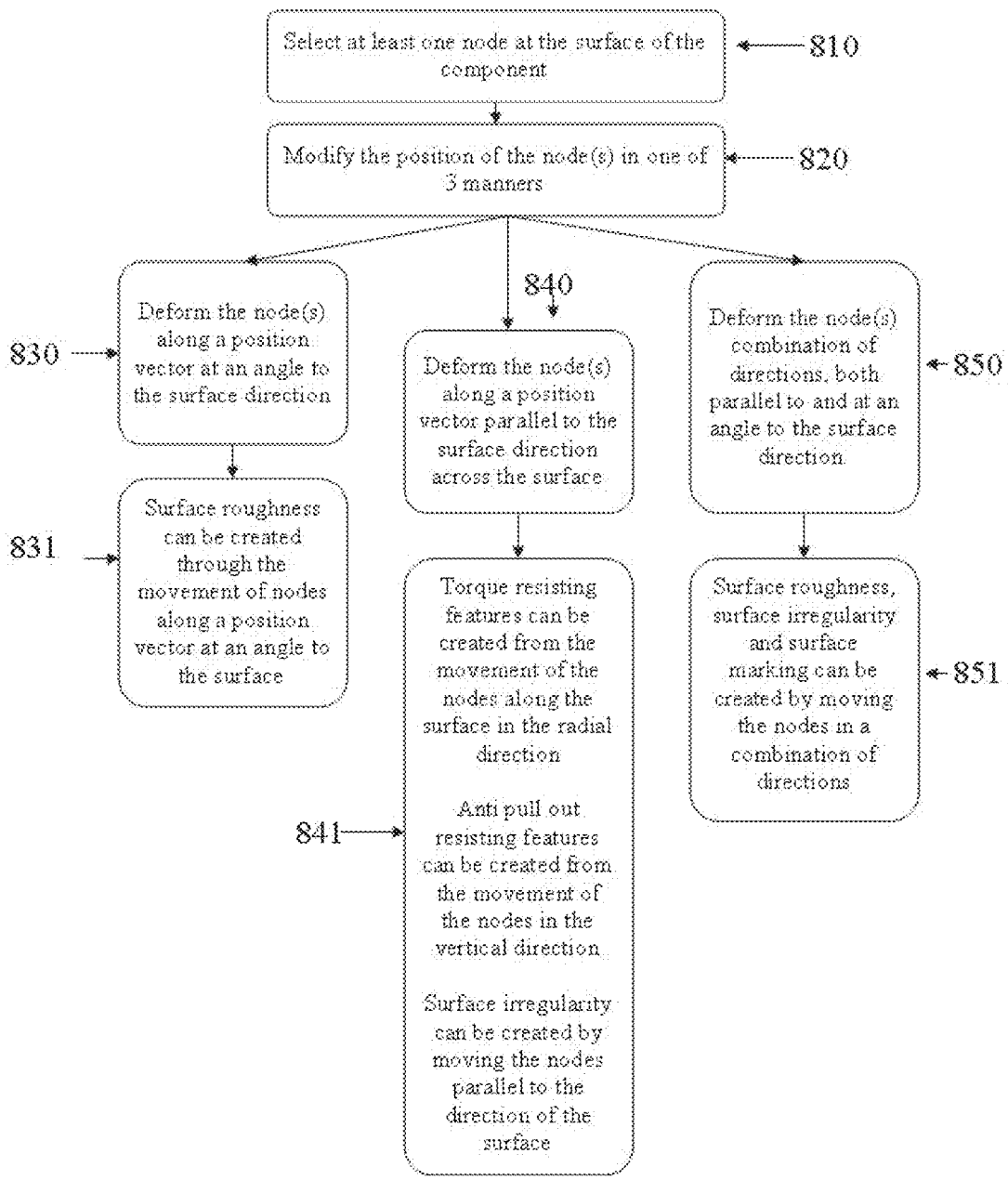
FIG. 31 is another process flow diagram in accordance with an embodiment of the invention.

A process flow diagram shown in FIG. 31 details an embodiment the creation of surface features through repositioning of nodes that lie on the boundary of the porous CAD volume. This operation can be performed on any porous geometry that consists of struts which interconnect at nodes along the boundary of the porous CAD volume.

At least one node is selected at a step 810 which can then be perturbed in a variety of ways to generate the desired surface properties. In one embodiment, a node along the boundary can be repositioned along a position vector which is at an angle to the surface direction as shown at steps 830-831. This process may be used to create surface properties such as surface roughness.

In another embodiment, a node can be moved along a position vector parallel to the surface direction across the surface which can be used to create torque or movement resisting, pullout resisting and surface irregularity properties at steps 840 and 841.

In yet another embodiment, any combination of the steps 830 and 840 may be used to create surface properties. Nodes can be moved both along and away from the surface to create areas of irregularity, roughness and marking at steps 850 and 851.

Figure 32:
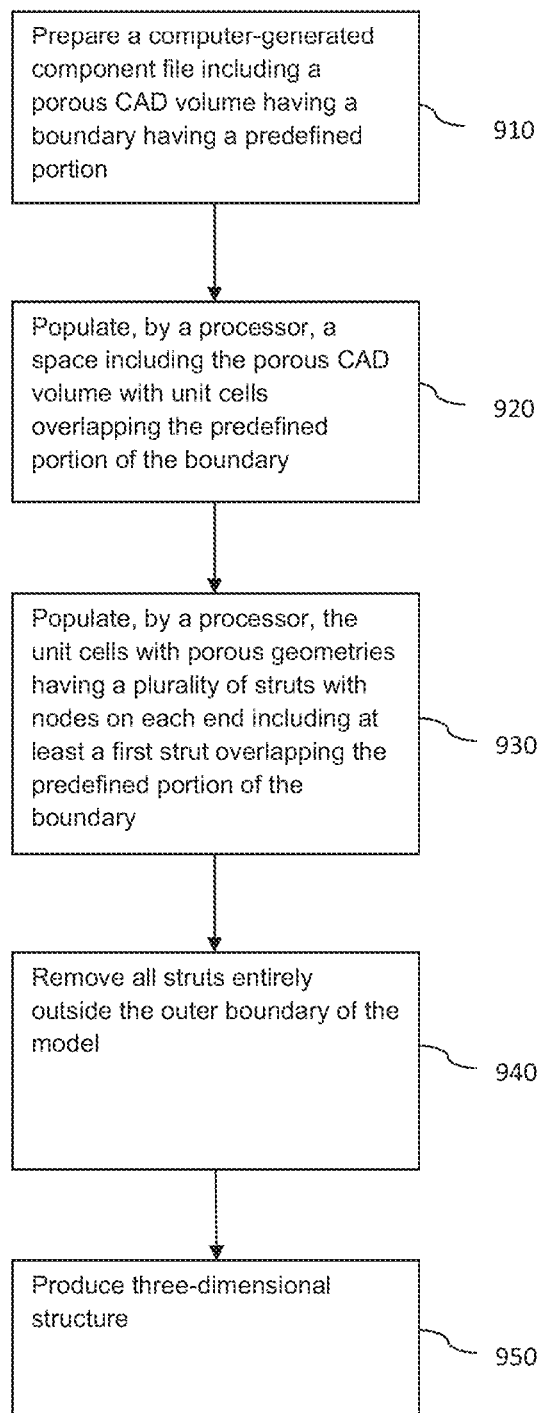
FIG. 32 is another process flow diagram in accordance with an embodiment of the invention.

In another example as shown in FIG. 32, a computer-generated component file is prepared at a block 910. The component file includes a porous CAD volume with a boundary having at least one predefined portion. At a block 920, a space that includes the porous CAD volume is populated, by a processor, with unit cells that overlap the predefined portion of the boundary. Such a space may be defined by sets of coordinates, such as Cartesian, polar, or spherical coordinates. At a block 930, the unit cells are populated with porous geometries. Within the porous geometries may be a plurality of struts. At least one end of the struts may have a node. As further shown at block 930, at least one of the struts overlaps the predefined portion of the boundary. Such a strut has a length, one node outside the porous CAD volume, and one node inside the porous CAD volume. At block 940, any struts entirely outside the predefined portion of the boundary are removed. In some embodiments, any struts outside the entire boundary are removed. In this manner, a computer-generated model of a three-dimensional structure constructed of porous geometries is prepared. At an optional block 950, a tangible three-dimensional structure having a shape corresponding to the computer-generated model may be produced. The shape of the three-dimensional structure may be in the form of a geometric lattice structure.

Visualization of all of the above effects under consideration can be achieved by voxelating the sliced output files from bespoke software that is being applied in an additive layer manufacturing machine. Utilizing developed algorithms and the output files, the data may be fed into a commercial software package, e.g., Matlab, and the images produced can be interpreted. FIGS. 2a and 2b illustrate an initial process operation in contrast to FIGS. 19a-19c, 20a-20c, 26a, and 26b representing common output images.

The approaches for generating three-dimensional models described herein may be used for building various tangible structures and surfaces, specifically structures and surfaces for medical implants. Although a brief summary follows, many details of the process of melting powdered metal are given in the '421 and '327 applications. In constructing a tangible structure from a model build structure, a layer of metal powder, in some instances, may be deposited on a substrate. The substrate may be a work platform, a solid base, or a core, with the base or core being provided to possibly be an integral part of the finished product.

The metal powder may be Ti alloys, stainless steel, cobalt chrome alloys, Ta or Nb. In some embodiments, individual layers of metal may be scanned using a directed high energy beam, such as a laser or e-beam system to selectively melt the powder, i.e., melt the powder in predetermined locations. Each layer, or portion of a layer, is scanned to create a plurality of predetermined porous geometries by point exposure to the energised beam. This leads to the production of struts that correspond to the struts described previously herein, as will be described below. Successive layers are deposited onto previous layers and also are scanned. The scanning and depositing of successive layers continues the building process of the predetermined porous geometries and oblique struts are directed to nodes. As disclosed herein, continuing the building process refers not only to a continuation of a porous geometry from a previous layer but also a beginning of a new porous geometry as well as the completion of the current porous geometry.

In a preferred aspect of the present invention, the high energy beam may be adjusted to modify the cross-sectional diameter of various struts. Some of the struts of the porous geometries may overlap struts of other porous geometries as a result of randomization within unit cells, but such struts never lose their identity with respect to their origin. Dimensions of strut diameter and unit cell size may enable the adjusting of the porosity throughout the completed structure. The strut diameter preferably should be nominally two times the diameter of the high energy beam, and each unit cell should have sides with lengths preferably no greater than 2 mm and have an aspect ratio that is limited to a maximum of 1:2 with respect to a maximum height of the unit cell.

In some embodiments, a component structure or substructure thereof produced by the approaches herein may be porous and if desired, the pores can be interconnecting to provide an interconnected porosity. In some embodiments, the amount and location of porosity may be predetermined, and preferably lie in the range 50% to 90% as being suitable when used as a bone ingrowth surface, and 20% to 90% as being suitable for polymer interlock surfaces. This also applies to cases where the outer porous section of a medical device is connected to host bone with bone cement or bone type adhesives for example. A base or core of cobalt chrome alloy, titanium or alloy thereof, stainless steel, niobium and tantalum, may be used to build a porous layer of any one of these metals and/or alloys by melting using high energy beam, such as a continuous or pulsed laser beam or an electron beam. Thus, a mixture of desired mixed materials can be employed. The porous layers can be applied to an existing article made from cobalt chrome, titanium or alloy, stainless steel, tantalum or niobium, such as an orthopedic implant. It is thus intended that the approaches described herein may be exploited to produce commercially saleable implants with bone in-growth structures having porous surfaces with a controllable texture or surface profile. Such an implant may be an acetabular component, a knee tibial or patella implant, a femoral knee or hip implant, or the like. The constructed medical implant may have a porosity and architecture optimised, to create very favourable conditions so that bone in-growth takes place in a physiological environment and the overall outcome favours long-term stability.

The medical implants, as well as other constructed structures, may be provided with an attaching mechanism for anchoring or at least more firmly attaching the medical implant to another element. One such example is an acetabular component being provided with a surface structure which mates with the surface of an augment component.

Because a laser melting process may not require subsequent heat treatment or the temperature at which this heat treatment occurs is lower than any critical phase change in the material, the initial mechanical properties of any base metal to which a porous structure is applied may be preserved.

The equipment used for the manufacture of such a device could be one of many currently available including but not limited to those manufactured by Renishaw, SLM Solutions, Realizer, EOS, Concept Laser, Arcam and the like. The laser or electron beam may also be a custom produced laboratory device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic implant comprising:
  a first implant structure corresponding to a computer-aided design model prepared by the steps of:
    preparing a computer-generated component file including a porous CAD volume having a boundary;
    populating, by a processor, a space including the porous CAD volume with unit cells on or overlapping the boundary;
    populating, by the processor, the unit cells with porous geometries, the porous geometries having a plurality of struts having opposing ends, each end being connected at a corresponding node, the plurality of struts including at least a first strut intersecting the boundary and having a length, one end connected at a first node at a first location either (i) on the boundary or (ii) outside the porous CAD volume, and another end connected at a second node at a second location either (i) on the boundary or inside the porous CAD volume when the first node is outside the porous CAD volume or (ii) inside the porous CAD volume when the first node is on the boundary, the length of the first strut being defined between the first and the second nodes;
    removing, by the processor, only all struts entirely outside the boundary of the porous CAD volume such that each end of the remaining struts remains connected at its corresponding node; and
    moving, by the processor, either (i) the first node of the first strut from the first location to a third location along the boundary in creating the computer-generated model of the three-dimensional structure or (ii) the second node of the first strut from the second location to a fourth location along the boundary in creating the computer-generated model of the three-dimensional structure such that the first strut has a different length than at least one strut adjacent to the first strut and such that each of the opposing ends of all of the struts are attached to an end of at least another one of the struts.

2. The orthopedic implant of claim 1, wherein, in preparing the computer-aided design model, when at least one adjacent strut adjacent to the first strut and inside the porous CAD volume is connected at the second node, a closer of the first node or the second node to the boundary is moved to the respective third or fourth location along the boundary.

3. The orthopedic implant of claim 2, wherein the computer-aided design model is further prepared by:
  when the first node is the closer node to the boundary, changing, by the processor, the length of at least the first strut such that the first strut remains connected at the first node; and
  when the second node is the closer node to the boundary, changing, by a processor, the length of the at least one adjacent strut such that the at least one adjacent strut remains connected at the second node.

4. The orthopedic implant of claim 1, wherein the computer-aided design model is further prepared by moving the one of the first node or the second node moved to the respective third or fourth location along the boundary to a location along the boundary nearest to the respective first location or second location or to a location along the boundary at which the first strut intersects the boundary prior to moving the one of the first node or the second node to the respective third or fourth location.

5. The orthopedic implant of claim 1, wherein, in preparing the computer-aided design model, at least a first set of the plurality of struts intersects the boundary, each of the struts of the first set of the plurality of struts having a length, an end at a first node, and another end connected at a second node, the computer-aided design model being further prepared by moving at least one of the first and the second nodes at which at least one of the struts of the first set of the plurality of struts is connected to a location to satisfy a predetermined surface roughness along the boundary.

6. The orthopedic implant of claim 5, wherein, in preparing the computer-aided design model, the nodes at which the first portion of the plurality of struts are connected are moved to locations selected at random along the boundary.

7. The orthopedic implant of claim 1, wherein, in preparing the computer-aided design model, the three-dimensional structure is configured to be placed into a separate structure, wherein the first node at which the first strut is connected is moved from the first location to the third location in a direction not parallel to the first strut to model the three-dimensional structure with a configuration for resisting movement of the three-dimensional structure when the three-dimensional structure is placed into the separate structure.

8. The orthopedic implant of claim 7, wherein, in preparing the computer-aided design model, each of the plurality of struts intersects the boundary, has a respective length, and has a respective first node at a respective first location either (i) on the boundary or (ii) outside the porous CAD volume, the computer-aided design model being further prepared by:
  moving a first node of at least a second strut of the plurality of struts in a second direction neither parallel to the second strut nor in the same direction as the movement of the first node of the first strut in modelling the three-dimensional structure with a configuration for resisting movement of the three-dimensional structure when the three-dimensional structure is placed into the separate structure.

9. The orthopedic implant of claim 1, wherein the computer-aided design model is further prepared by forming a strut extending from the first node at which the first strut is connected in order to either one or both of (i) produce a rougher surface of the three-dimensional structure and (ii)

produce interlocking features to enable assembly or engagement with at least one additional three-dimensional porous structure.

10. The orthopedic implant of claim 1, wherein, in preparing the computer-aided design model, each of the plurality of struts intersects the boundary, each of the plurality of struts having a respective length and an end connected at a respective first node at a respective first location either (i) on the boundary or (ii) outside the porous CAD volume, the computer-aided design model further prepared by:
    moving first nodes at which respective struts of a first set of struts of the plurality of struts is connected in a direction away from the boundary.

11. The orthopedic implant of claim 10, wherein, in preparing the computer-aided design model, the first nodes at which the respective struts of the first set of struts correspond to at least portions of an identifying marker of the three-dimensional structure visible to the unaided eye when formed.

12. The orthopedic implant of claim 10, wherein, in preparing the computer-aided design model, the first nodes at which the respective struts of the first set of struts correspond to at least portions of an identifying marker of the three-dimensional structure invisible to the unaided eye when formed.

13. The orthopedic implant of claim 1, wherein the computer-aided design model is further prepared by:
    populating, by a processor, the space with at least one elongated fixation element attached to one of the porous geometries and extending beyond the boundary.

14. The orthopedic implant of claim 1, wherein in preparing the computer-aided design model, the component file further includes a solid CAD volume contacting and extending along a portion of the porous CAD volume, and wherein the computer-aided design model is further prepared by:
    populating, by a processor, the space with at least one elongated fixation element extending from the solid CAD volume and through the porous CAD volume.

* * * * *